United States Patent [19]

Lewis et al.

[11] Patent Number: 5,447,687
[45] Date of Patent: Sep. 5, 1995

[54] LUMINOMETER

[76] Inventors: Scott C. Lewis, 864 Crosse Ave., Amherst, Ohio 44001; Stefan R. Pabst, 21484 Hawley Rd., Wellington, Ohio 44090

[21] Appl. No.: 366,003

[22] Filed: Dec. 29, 1994

Related U.S. Application Data

[63] Continuation of Ser. No. 35,341, Mar. 19, 1993, abandoned.

[51] Int. Cl.[6] .............................................. G01N 21/76
[52] U.S. Cl. .................................. 422/52; 250/361 C; 250/367
[58] Field of Search ............... 422/52, 68.1; 436/171, 436/172, 180; 250/361 C, 367; 356/244, 246, 440

[56] References Cited

U.S. PATENT DOCUMENTS

| | | | |
|---|---|---|---|
| 4,099,920 | 7/1978 | Heiss | 422/52 |
| 4,319,842 | 3/1982 | Priarone et al. | 356/317 |
| 4,372,745 | 2/1983 | Mandle et al. | 436/537 |
| 4,563,331 | 1/1986 | Losee et al. | 422/52 |
| 4,755,055 | 7/1988 | Johnson et al. | 356/440 |
| 4,778,763 | 10/1988 | Makiguchi et al. | 422/52 X |
| 4,943,159 | 7/1990 | Oetliker et al. | 250/458.1 |
| 5,043,141 | 8/1991 | Wilson et al. | 422/52 |
| 5,082,628 | 1/1992 | Andreotti et al. | 422/82.08 |
| 5,089,630 | 2/1992 | Bronstein et al. | 549/220 |
| 5,096,807 | 3/1992 | Lesback | 435/6 |
| 5,139,745 | 8/1992 | Barr et al. | 422/82.08 X |
| 5,223,218 | 6/1993 | Fukuoka et al. | 422/52 |

FOREIGN PATENT DOCUMENTS 2233450 9/1991 United Kingdom .

*Primary Examiner*—Jeffrey R. Snay
*Attorney, Agent, or Firm*—Judith A. Roesler; Nicholas I. Slepchuk, Jr.; Arthur S. Morgenstern

[57] ABSTRACT

A method and apparatus for determining a plurality of substances or constituents of a specimen sample includes the steps of placing a single specimen sample in a reaction vessel or test tube and adding at least two reagents to the reaction vessel to form a detectable product and then initiating a reaction within the vessel and provide an emission of light energy in a predetermined spectral range. The reaction vessel is disposed in a chamber of a housing and a plurality of detector assemblies are disposed about the housing with portions of the detector assemblies disposed through the housing and exposed to the reaction vessel. Each of the detector assemblies receives a portion of the light emission and feeds such portion to a detector. Each of the detectors detect the existence of light emissions in one of a plurality of spectral ranges and feeds that information to processing circuitry to provide data for determining the presence of a specific specimen substance(s) or constituent(s) based upon the detected luminescence.

24 Claims, 37 Drawing Sheets

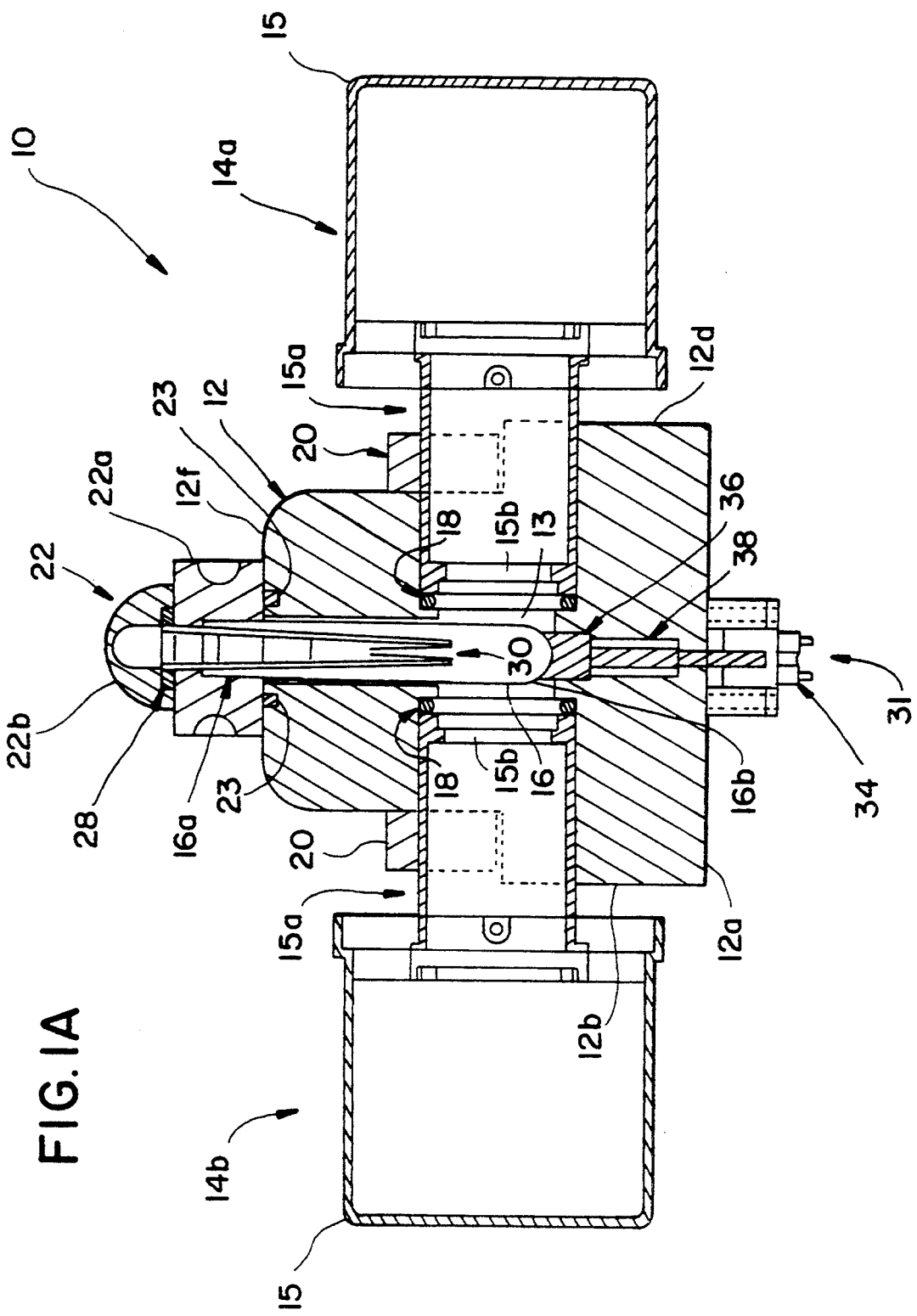

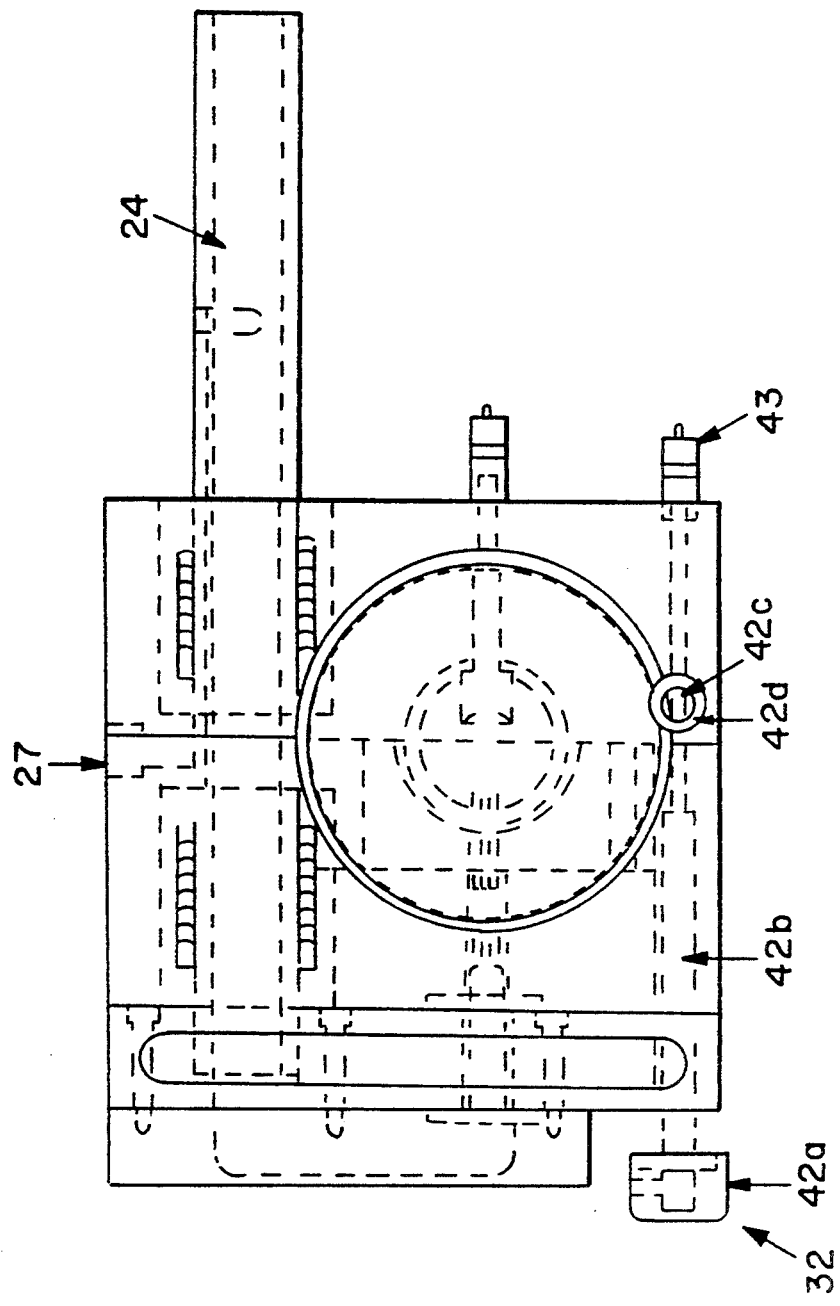

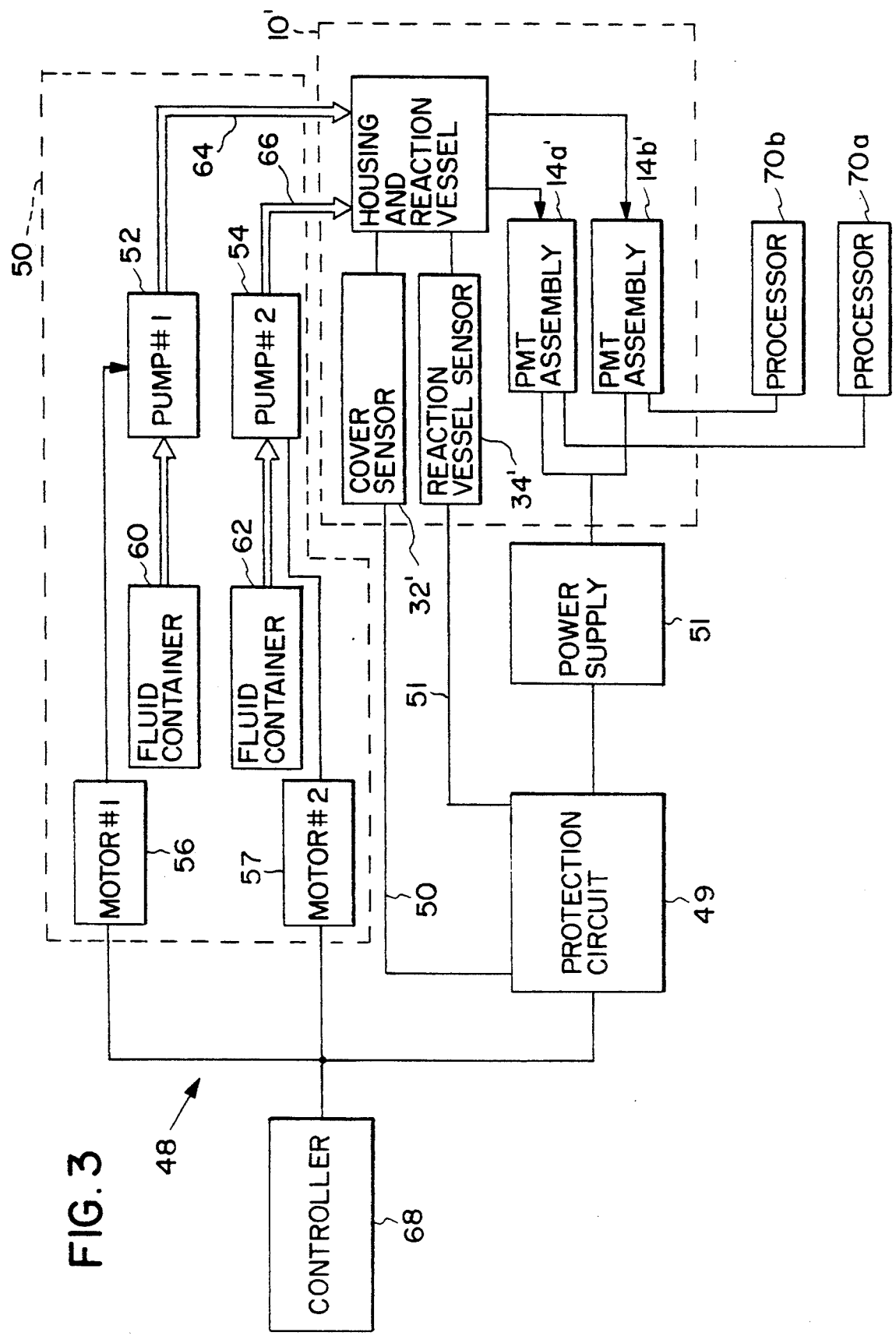

DMAE-Bz

DIPAE-Bz

3-MeO-DMAE-Bz

ABAC-Bz

LEAE-Bz

DIP-LEAE-Bz

LEAC-Bz

3-EtO-LEAE-Bz

3-QAE-LEAE-Bz

2-MeO-LEAE-Bz

2-QAE-LEAE-Bz

NSP-LEAE-Bz

2-MeO-NSE-LEAE-NHS

2-MeO-LEAE-Imidate

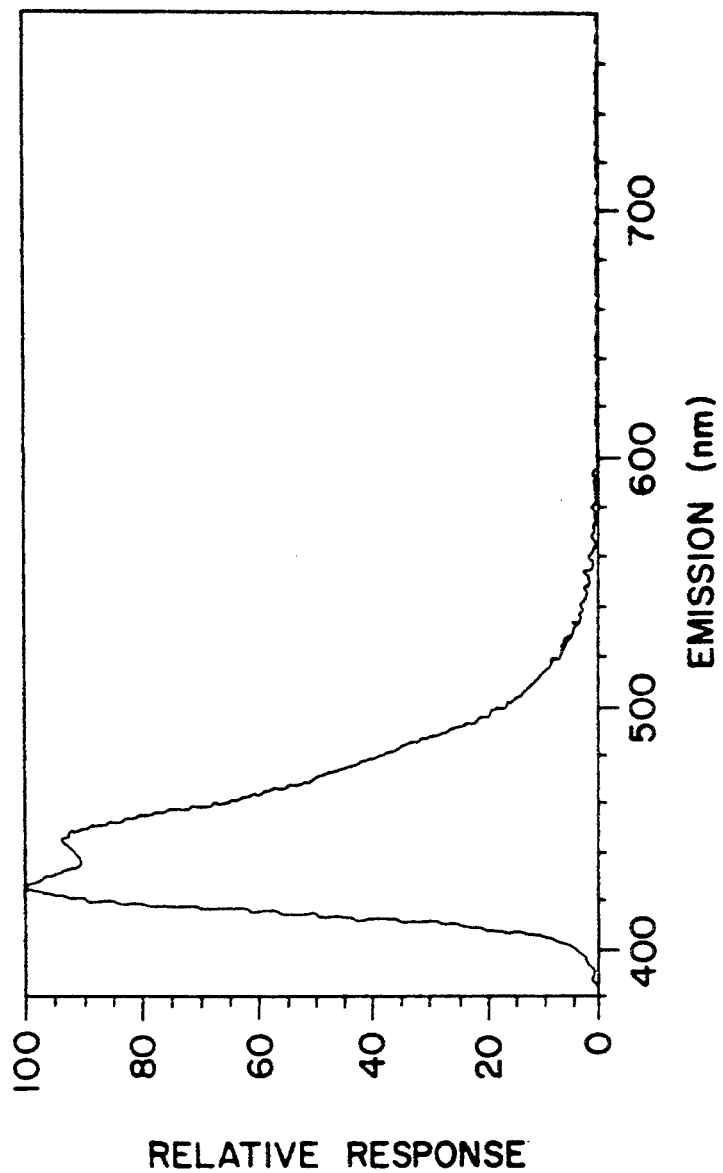

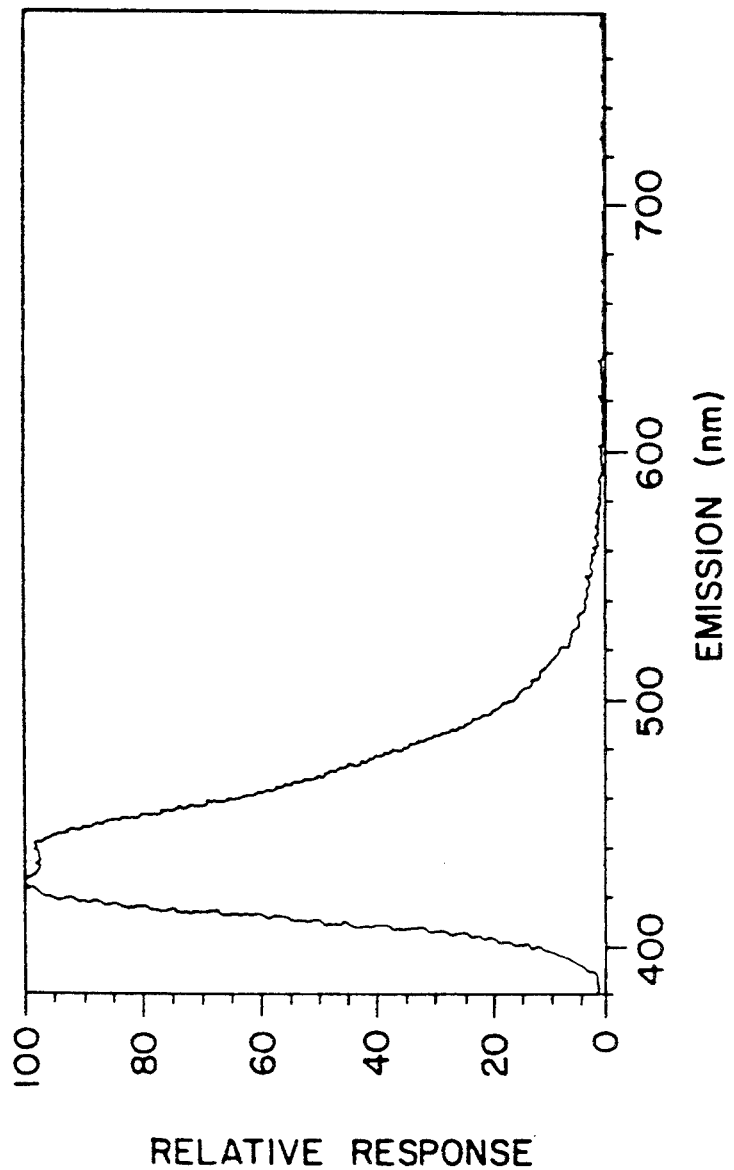

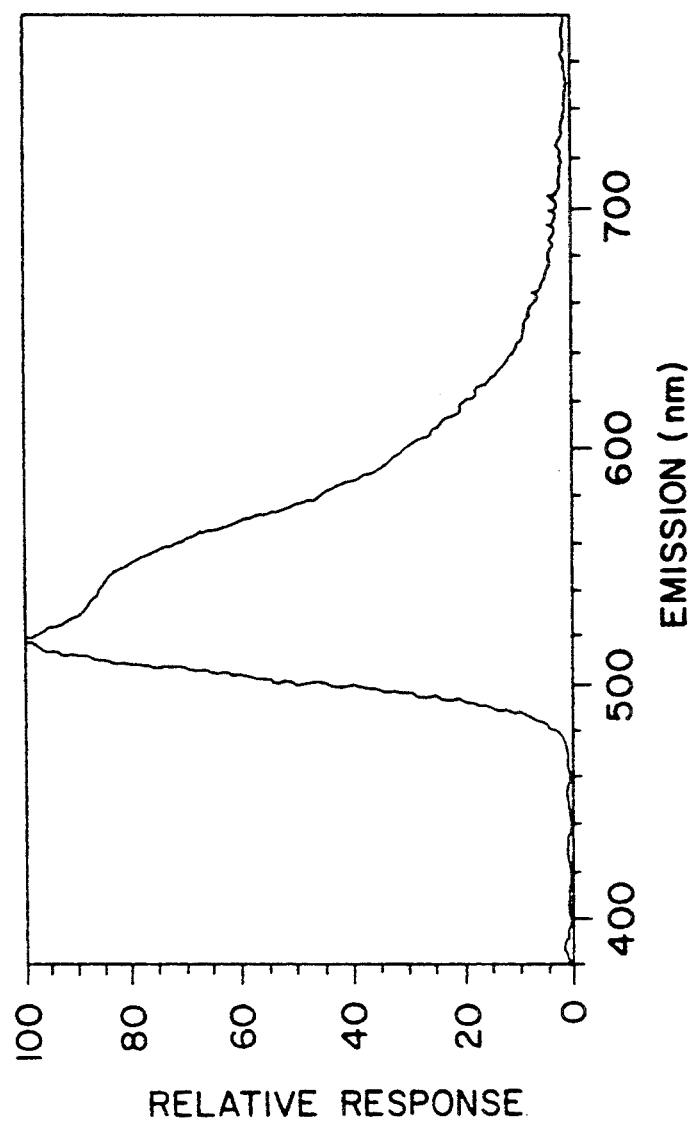

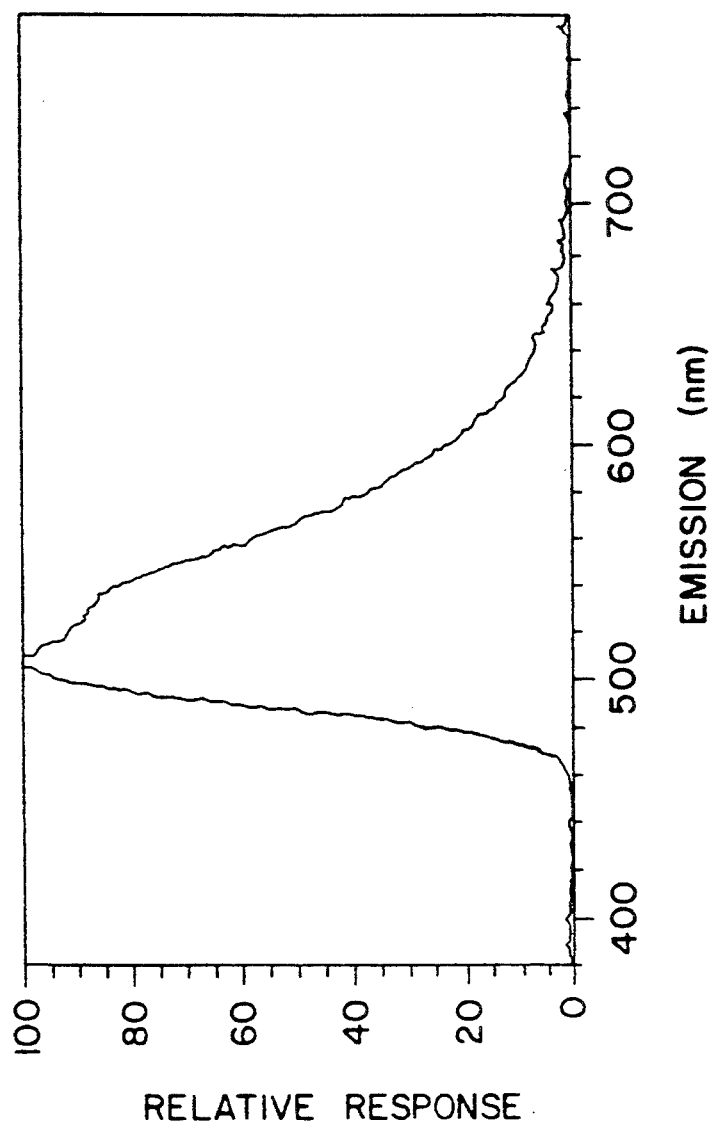

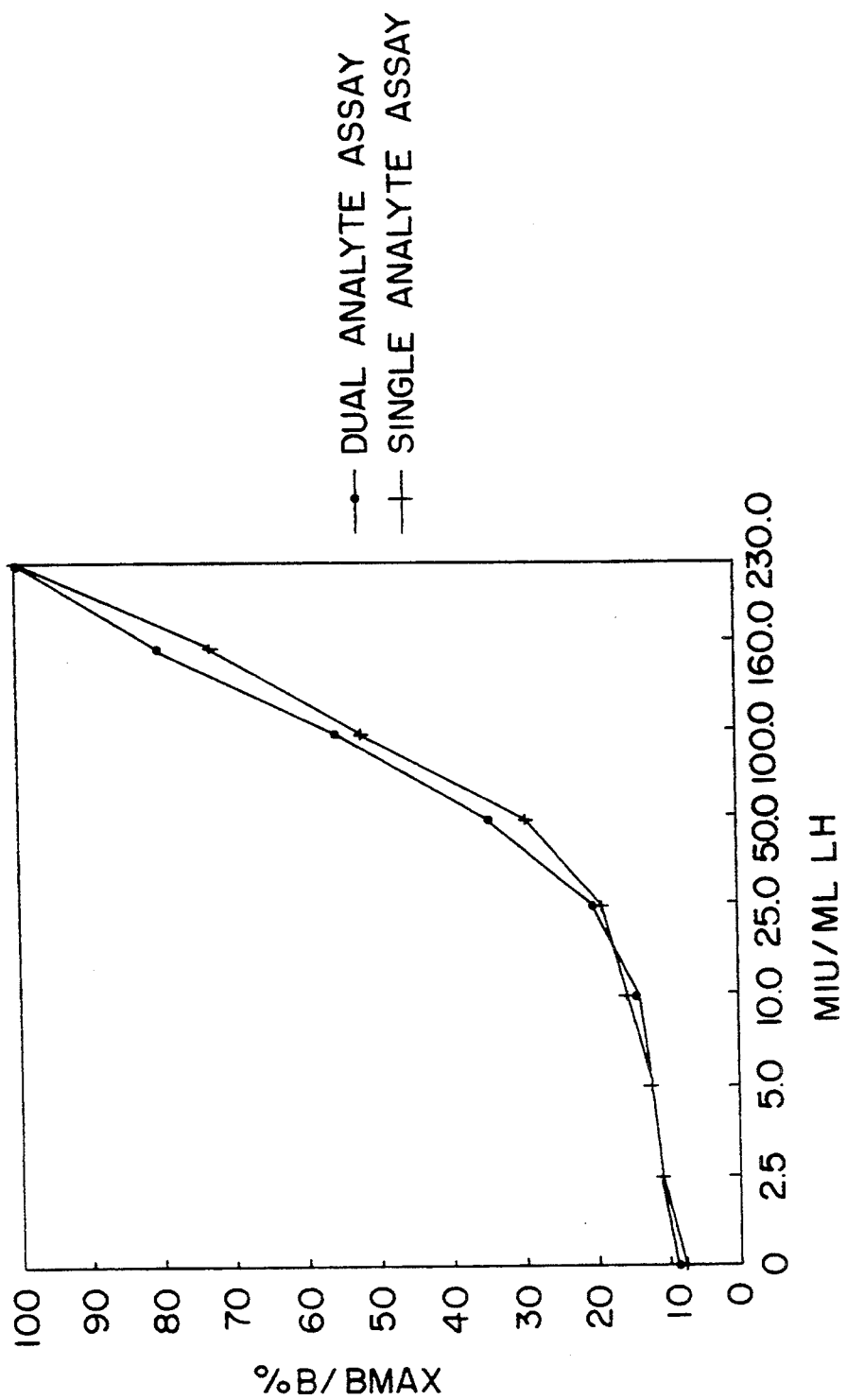

LUMINOMETER

This is a continuation of application Ser. No. 08/035,341 filed on Mar. 19, 1993, now abandoned.

FIELD OF THE INVENTION

This invention relates to specimen testing apparatus and more particularly to luminometers.

BACKGROUND OF THE INVENTION

As is known in the art, systems which may be used to test specimen samples such as blood samples, for example, add a single reagent to the sample in a chamber. The reagent reacts with the sample and cause the sample to emit light or to form a detectable product which, on further treatment, will emit light. Depending upon the presence of the constituent(s) of the sample a corresponding spectral distribution of the emitted light is provided. Furthermore, depending upon the specimen sample and the reagent added thereto the resultant luminescence occurs in a predetermined spectral range. The light emissions may be fed through a spectral filter and subsequently coupled to a photomultiplier tube and detector. Thus, with knowledge of the type of specimen sample, the type of reagent and the resultant spectral representation it is possible to determine the presence of certain substances in the specimen sample. Separate tests may be run with different reagents in the separate chambers to test for other constituents in the specimen.

SUMMARY OF THE INVENTION

It may in some applications, however, be desirable to provide a system in which a plurality of reagents may be added to a single chamber and a detection system simultaneously detects light emission in a plurality of different spectral ranges. Thus according to the present invention, specimen analysis is enhanced by applying at least two reagents to the same specimen sample in a specially adapted chamber and using a plurality of detectors to simultaneously detect the chemiluminescence in separate spectral ranges caused by the reaction with one or more substances of the specimen. The reagents react with the sample substances and are further treated to provide substantially non-overlapping luminescence signals which may be sensed by the detectors and separately processed to determine the constituents or substances of the specimen sample.

Thus in accordance with the present invention, a testing apparatus includes a housing having a chamber. A reaction vessel is disposed through a bore in a top wall region of the housing and retained in a predetermined location in the chamber. A plurality of detector assemblies are disposed about the housing with each one of such detector assemblies disposed through a corresponding bore provided in corresponding side wall regions of the housing such that the reaction vessel is exposed to the detector assemblies. In accordance with this particular arrangement, a luminometer capable of detecting one or more substances of a specimen sample having a resultant luminescence in a plurality of separate spectral ranges is provided. The reaction vessel may be provided, for example, as a cuvette or a test tube. Into the reaction vessel may be added a specimen sample and a plurality of luminescent reagents or conjugates reagents. The reagents are selected such that they interact with the sample but not with each other. The reagents react with the sample to provide, from the sample, a product which, upon further treatment, results in light emissions in a plurality of different spectral ranges. The detector assemblies may include, for example, photomultiplier tubes (PMTs). Each of the plurality of PMTs may provide a response to a chemiluminescent flash produced in the reaction vessel. A first one of the PMTs may respond to light emissions in a first spectral range and a second one of the plurality of PMTs may substantially simultaneously respond to light emissions in a second spectral range. Thus, the luminometer may detect, in a single test, light emissions in at least two different spectral ranges. The testing apparatus may also be provided having a fluid injection system coupled to the housing through a dispense tube to thus provide the testing apparatus having fluid control capabilities. The fluid injection system may be used to add acid and/or base fluid to the reaction vessel. Thus, vessels which are prepared to have acid and/or base fluids added thereto may be disposed in the housing and the fluid injection system may be used to add the requisite type and amount of fluid to the reaction vessel. Furthermore a processor may be coupled to the fluid injection system to control the timing and amount of fluid introduced into the reaction vessel via the fluid injection system. Moreover, the processor may also control the timing with which tests are conducted in the testing apparatus.

The testing apparatus may also be provided with an automated means for advancing vessels to the detector assemblies and following the luminescent flash, removal from the apparatus.

BRIEF DESCRIPTION OF THE DRAWINGS

The foregoing features of this invention as well as the invention itself may be more fully understood from the following detailed description of the drawings in which:

FIG. 1A is a cross sectional view of the luminometer assembly taken along lines 1A—1A of FIG. 1;

FIG. 1C is a side view of the luminometer assembly taken along lines 1C—1C of FIG. 1;

FIG. 3 is a block diagram of a luminometer assembly having a fluid injection system.

FIGS. 5A–5E illustrate emission spectra of acridinium esters and ABAC.

FIGS. 6A–6J illustrate emission spectra of LBAC.

FIG. 12 illustrates LH standard curve assays read on a dual PMT luminometer.

DESCRIPTION OF THE PREFERRED EMBODIMENTS

Figure 1:
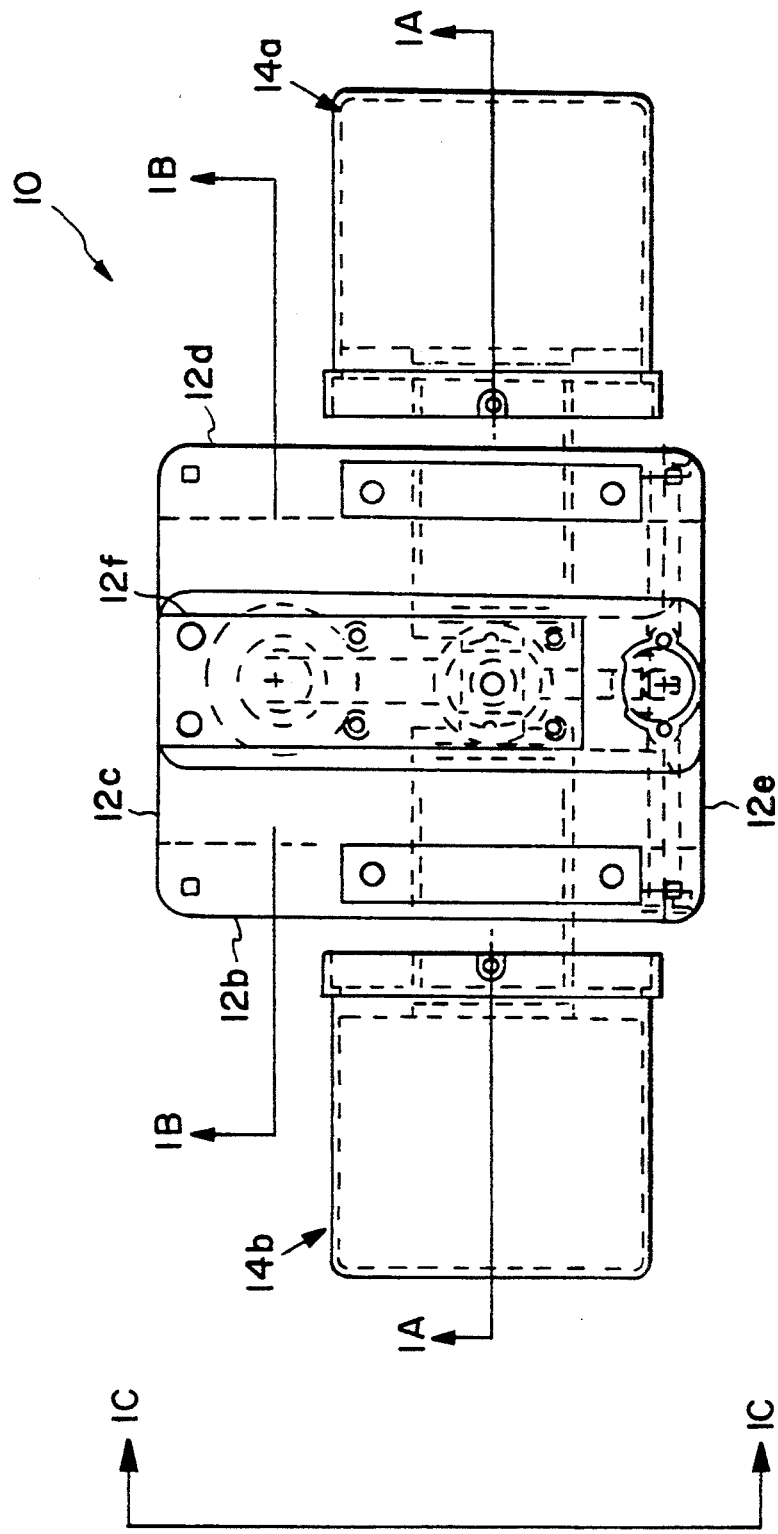
FIG. 1 is a top view of a luminometer assembly.

Referring now to FIGS. 1–1C in which like elements are provided having like reference designations throughout the several views, a luminometer assembly 10 includes a main housing 12 having a base region 12a, side wall regions 12b, 12c, 12d, 12e and a top region 12f. The base, side wall and top regions are provided having continuous portions such that the housing 12 provides a chamber 13 in which a reaction may take place. A plurality of photomultiplier tube assemblies may be disposed in the sidewall regions of the housing 12, a pair of such photomultiplier tube assemblies 14a, 14b here being shown disposed in opposing side wall regions 12b, 12d of the housing 12.

Each of the photomultiplier tube assemblies 14a, 14b includes an aluminum housing 15 in which may be disposed a conventional photo-multiplier tube and a conventional amplifier/discriminator board. The photo-multiplier tubes (PMTs) may be provided as, but are not limited to, the types having side-on photocathodes, end-on photocathodes or a combination of both side-on and end-on photocathodes. Suffice it to say that PMTs disposed in the photomultiplier tube assemblies 14a, 14b may preferably be selected having optimum spectral sensitivity in the wavelength range of emissions of the chemiluminescent compound(s) to be detected and/or quantitated.

The aluminum housing 15 includes a nosepiece 15a having a quartz window 15b disposed therein. Alternatively, the nosepiece 15a may be provided having a filter (not shown) disposed therein in addition to or in place of the quartz window to thus optimize the performance of the corresponding PMT assembly. Such filters may preferably be disposed between the photocathode and the reaction vessel and such filters may preferably be provided having filter characteristics which selectively allow chemiluminescent emissions in predetermined spectral ranges to pass therethrough. Thus the filters may preferably be provided having bandpass filter characteristics. However, the filters may alternatively be provided having lowpass, highpass, stopband, or any other filter characteristics well known to those of ordinary skill in the art.

Such filters may be provided having filter characteristics which provide a relatively low insertion loss to light having wavelengths less than 500 nanometers (nm). Filters having such filter characteristics may be provided, for example, as one of the types manufactured by Corion corporation and identified as part number P70-450 or part number LS-500.

Alternatively such filters may also be provided having filter characteristics which provide a relatively low insertion loss to light having wavelengths greater than 500 nanometers (nm). Such filters may be provided, for example, as the type manufactured by Corion corporation and identified as part number LL-500. Thus simultaneous emission of two distinct spectra may be separately detected by distinct, appropriately filtered PMT's.

Since spectral transmittance overlap is a source of "crosstalk" between the detectors and corresponding chemiluminescent compounds, the filters should generally be provided having filter characteristics selected to minimize any spectral overlap in spectral transmittance. It is, however, most desirable to have a pair of chemiluminescent compounds with no spectral overlap in spectral transmittance to thus provide a system having a minimum amount of crosstalk, or to appropriately correct for spectral overlap.

A reaction vessel 16 is disposed through the top region 12d of the housing 12 and extends into the chamber 13 such that opposite sides of the vessel 16 are exposed to a corresponding one of the photomultiplier tube assemblies 14a, 14b. The reaction vessel 16 may be provided for example as a cuvette or test tube or any other vessel well known to those of ordinary skill in the art.

The side wall regions 12b, 12d of the main housing 12 are provided having counterbores therethrough. An O-ring 18 is disposed at the bottom of each of the counter bores and the PMT assemblies 14a, 14b are disposed with a predetermined force in the counterbores against a corresponding one of the O-rings 18a, 18b such that the nosepiece 15a extends into the housing 12. The O-rings 18 prevent light from passing through the interface between the PMT assemblies 14a, 14b and the housing 12 and thus minimize the amount of external light provided to the chamber cavity 13. Each of the PMT assemblies 14a, 14b may be held in place by a corresponding clamp 20. Each of the clamps 20 are disposed and tightened about the circumference of a corresponding one of the PMT assemblies 14a, 14b.

A top cover assembly 22 is disposed on the main housing 12 over a first end of the reaction vessel 16. The top cover assembly 22 is coupled to and aligns a probe assembly 28 in a predetermined location of the reaction vessel 16 and provides an opening through which the reaction vessel 16 may be inserted and removed from the main chamber 13.

The probe assembly 28 will be described more fully below in conjunction with FIG. 2. Suffice it here to say that the top cover assembly 22 is connected to the probe assembly 28 and the probe assembly 28 may be disposed in the reaction vessel 16 to position at least one dispense probe 30 at a predetermined height above a final liquid height in the reaction vessel 16.

Figure 1B:
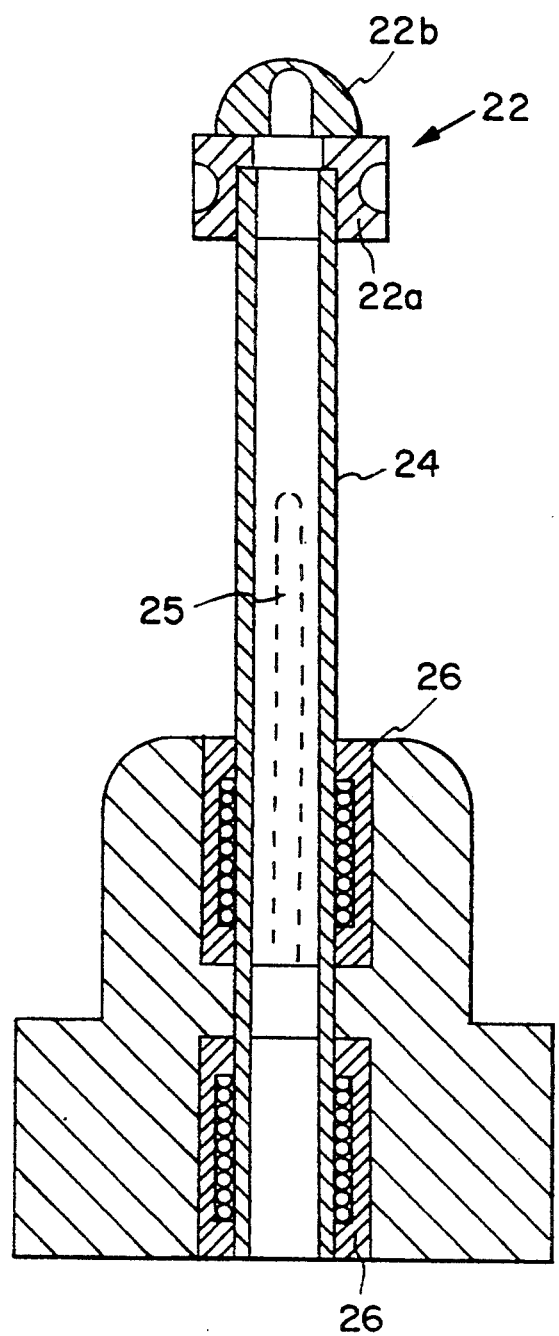
FIG. 1B is a cross sectional view of the luminometer assembly taken along lines 1B—1B of FIG. 1.

The top cover assembly 22 (shown in FIG. 1 in the closed position and FIG. 1A in the open position) includes a cover body 22a and a cover plate 22b. The cover assembly 22 is connected to a shaft 24 (FIG. 1A) through a pin, and thus securely connects the cover assembly 22 to the shaft 24. The shaft 24 operates along two linear bearings 26 (FIG. 1B), thus allowing the shaft 24 to move in both the radial and rotational directions.

The shaft 24 has here been provided having on a surface thereof an axial groove 25 having a predetermined length and a predetermined width. At one end of the shaft 24 the groove 25 rotates 90 degrees and follows a path in a direction along the circumference of the shaft 24 for a predetermined distance, here the distance corresponds to 90 degrees of rotation. A pin (not shown) may be connected to the main housing 12 at location 27 (FIG. 1C). The pin is disposed in the groove 25 to thus limit the mechanical travel of the shaft in an axial direction as determined by the groove length. The pin also limits the mechanical travel of the shaft 24 in a circumferential direction as determined by the circumferential length of the groove 25. Thus the groove/pin combination provides the probe assembly 28 and top cover assembly 22 having a predetermined amount of movement selected such that the reaction vessel 16 may easily be inserted and removed from the chamber 13.

To reduce measurement errors, it is desirable to shield the reaction and thus the reaction vessel from ambient light. It is thus desirable to provide the chamber 13 as a light tight chamber 13.

To provide a light seal between the top cover 22 and the main housing 12, the main housing 12 is here provided having a first surface with a groove therein, such groove being provided in a surface of the housing in a region and pattern which substantially circumscribes the reaction chamber 13. A corresponding lip 23 may be provided in the top cover assembly 22, such that the lip 23 may be disposed in the groove to provide a region in which light may be trapped when the cover 22 is placed in its closed position. When the top cover assembly 22 is placed in its closed position, the assembly 22 provides a light tight seal against the main housing 12. When the PMT assemblies 14a, 14b are disposed in the housing bores against the O-rings 18 and the top cover assembly 22 is disposed on the housing 12 and placed in its closed position, light is prevented from entering the chamber 13 and the chamber 13 is thus provided as a light tight chamber.

Figure 2:
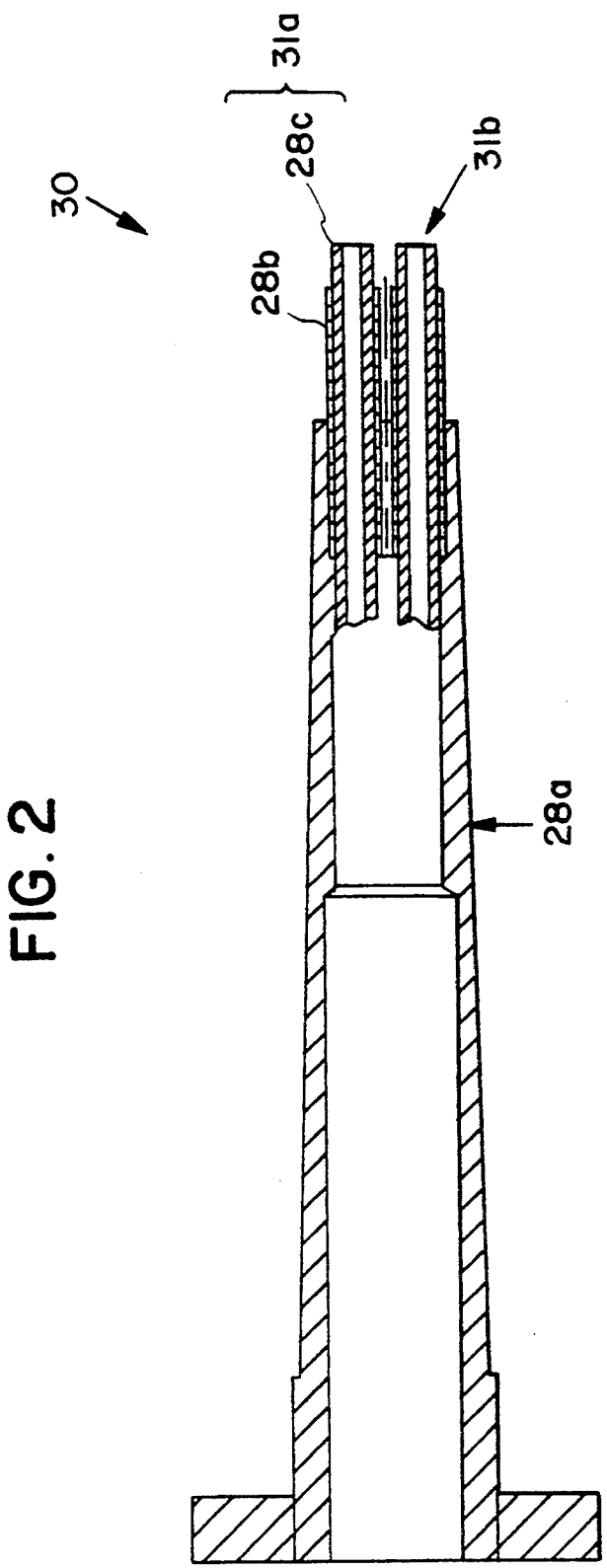
FIG. 2 is a partial cross sectional view of a probe assembly which may be of the type used in the luminometer of FIG. 1.

Referring briefly to FIG. 2, the probe assembly 28 includes a probe body 28a which may preferably be lightly press fit into an opening of the top cover body 22a (FIG. 1) and held in place by the cover plate 22b (FIG. 1). The probe body 28a locates into a shouldered area of the top cover body 22c (FIG. 1) thus assuring proper orientation and positioning of the probes 30.

Portions of the probe body 28a have here been removed to reveal that the probe assembly 28 further includes a plurality of dispense probes 30. Each of the dispense probes 30 is provided from a guide tube 28b and a dispense tube 28c. The guide tube 28b may be provided, for example, as stainless steel tube press fit into the probe body 28a to secure the tube 28c in a predetermined location. The tube 28c provides a dispense port for acid and base solutions and thus may be provided from any dielectric material such as plastic, Teflon (TM) or any other dielectric or non-dielectric material well know to those of ordinary skill in the art. The tube 28c is provided having an outside diameter which is slightly larger than the inside diameter of the corresponding guide tube 28b, to provide a slight interference fit between tubes 28b and 28c to thus securely hold the tube 28c in the predetermined location.

Referring again to FIGS. 1-1C, the system 10 further includes a reaction vessel sensor assembly 31 and a cover sensor assembly 32 which are coupled to the main housing 12 and operate to maintain the chamber 13 as a light-tight environment and to prevent damage to the PMT assemblies 14a, 14b during operation of the system 10.

The reaction vessel sensor assembly 31 provides an indication to confirm that a vessel is disposed in the chamber 13. The reaction vessel sensor assembly 31 includes a sensor 34, a reaction vessel sensor flag 36, and a spring 38. The reaction vessel sensor flag 36 provides two functions.

The first function is to assist in centrally locating the reaction vessel 16 in the chamber 13. It is desirable to centrally locate the reaction vessel 16 within the chamber 13 to provide an equal distance from each PMT 14, 14b to the corresponding side of the reaction vessel 16. The reaction vessel 16 may be centrally located, for example, by providing the reaction vessel sensor flag 36 having a first end in which a spherical socket is provided. The spherical radius of the socket may be selected to correspond to the spherical radius of a second end 16b of the reaction vessel 16.

The second function of the flag 36 is to interrupt the sensor 34 when the reaction vessel 16 is inserted into the chamber 13 and the top cover 22 is properly closed. The flag 36 interrupts the sensor when the vessel 16 is properly located on the sensor flag 36. The sensor flag 36 is disposed over the spring 38 which exerts a spring force in the up direction on the vessel 16. This causes the reaction vessel 16 to protrude out of the main body 12. When the top cover assembly 22 is lowered onto the main body 12 the top cover assembly 22 exerts a force in the down direction upon the reaction vessel 16. Likewise, the reaction vessel 16 forces the sensor flag 36 down against the spring force. The bottom of the sensor flag 36 is forced into the path of the optical sensor 34 and interrupts the optical path of the sensor. Consequently the optical sensor 34 provides a signal that the reaction vessel 16 is properly loaded into the chamber 13.

The cover sensor assembly 32 is coupled to a spring loaded latch 40 disposed on the front of the housing 12 and senses whether the cover 22 is securely closed. The cover sensor 32 assembly includes a spring loaded flag activated by an optical switch when a vessel 16 is present in the chamber 13. When the sensor 32 is activated, a first LED will turn on. This sensor may help to prevent dispensing acid or base into the chamber when no vessel is present.

The latch 40 is here implemented via a recess in the front of the housing in which a shaft 42 is disposed. The latch 40 provides two functions; first, it holds the top cover 22 in the closed position, thus pushing the vessel 16 down and activating the reaction vessel sensor 31 and second, the latch 40 provides a mechanism to activate the cover sensor 32 only after the cover 22 is in its closed position to provide a light tight seal. The cover sensor 32 may be coupled to the LED 42 and to an electrical logic circuit relay (not shown) which controls power to the PMT assemblies 14a, 14b. Thus, when the sensor 32 is placed in its open position, no voltage is provided to the PMT assemblies 14a, 14b. The sensors, therefore, assist in preventing the PMT assemblies 14a, 14b from being exposed to excessive light. Furthermore, the sensor assemblies 31 and 32 protect the PMT assemblies 14a, 14b against inadvertent exposure to light while power is applied thereto. This reduces the settling time of the assemblies 14a, 14b.

The cover sensor assembly 32 includes a knob 42c disposed over a first end of a cover sensor shaft 42b. The knob 42a may be secured to the cover sensor shaft 42b with, for example, a set screw or any other like means and provides an easy grip with which an operator may use the sensor assembly 32. A pair of ball bearings 42c having grooves of a predetermined depth provided in an outer surface thereof are coupled to a cover sensor swing shaft 42d. The cover sensor assembly 32 further includes an optical sensor 43 disposed about a second end of the cover sensor shaft 42b. The cover sensor shaft 42b is press fit into the cover sensor swing shaft 42d. The cover sensor swing shaft 42d may thus rotate about the axis of the cover sensor swing shaft 42d.

As may be most clearly seen in FIG. 1C when the cover sensor shaft 42b is placed in a vertical position (that is having a longitudinal axis parallel to the longitudinal axis of probe 30), the knob 42 prevents the cover 22 from being opened and exposing the cavity 13 and thus the reactor vessel 16 and powered up PMT assemblies 14a, 14b to ambient light. Furthermore, when the shaft 42b is engaged in a vertical position, the second end of the cover sensor shaft 42b interrupts the optical sensor 43, thus signaling that the top cover 22 is properly closed. When the sensor 43 is interrupted, power may be applied to the PMT assemblies 14a, 14b. When the cover sensor shaft 42b is rotated such that the knob 42a moves away from the cover 22, the knob 42a releases the top cover assembly 22, thus allowing the top cover assembly 22 to be opened.

Once the cover sensor shaft 42b and knob 42a have moved a distance such that the shaft 42b has sufficiently cleared the top cover assembly 22, the optical sensor 43 is provided in an unblocked condition. That is, the optical sensor 43 does not detect any interruptions. When this occurs, power is removed from the PMT's 14a, 14b thus preventing operation of the system 10.

Disposed on the housing 12 are three light emitting diodes (LEDs) 46a, 46b and 46c, generally referred to as 46. LED 46a is coupled to the reaction vessel sensor 34. Thus when the vessel 16 is disposed into the chamber 13 and the cover 22 is placed in its closed position, power is fed to the LED 46c and the LED 46c thus emits a light to indicate that the reaction vessel is in the chamber 13.

The second LED 46b is coupled to the cover sensor 32. When the spring loaded latch 40 is positioned in the vertical position, thus closing the latch 40, power is fed to the LED 46b which thus emits a light to thus indicate the cover 22 has been placed in its closed position.

When both the reaction vessel and the cover sensor LED's 46a, 46b are activated, the LED 46c emits a light to thus indicate that the system 10 is properly prepared to perform a test.

As will be described further below in conjunction with FIG. 3, once a test has been completed, the vessel 16 should be removed from the chamber 13. Upon completion of a test, if the cover 22 has not been opened and or the vessel 16 has not been removed from the chamber 13, a protection circuit prevents the system 10 from operating.

Referring now to FIG. 3, a testing apparatus 48 includes a luminometer assembly 10', which may be similar to the luminometer assembly 10 described above in conjunction with FIGS. 1–1C, and a protection circuit 49 which may be provided as a processor, an analog logic circuit, a digital logic circuit or by any other means well known to those of ordinary skill in the art. The protection circuit is coupled to a power supply 51 which provides power to the PMT assemblies 14a', 14b'. The protection circuit 49 is also coupled to sensors 32', 34' and prevents operation of the testing apparatus 48 unless predetermined conditions have been met.

Each sensor 32', 34' provides a sensor signal (i.e. cover 22 opened and reaction vessel 16 removed from chamber 13) on a corresponding one of the signal paths 50, 51 to the protection circuit 49. To test for the requisite conditions, the protection circuit 49 analyzes the sensor signals and provides a protection signal in response thereto. If the sensors 32', 34' indicate either that the cover 22 (FIG. 1A) has not been opened or that the vessel 16 (FIG. 1) has not been removed from the chamber 13 (FIG. 1) then the protection signal prevents operation of the system 10'. This is necessary to prevent fluid (e.g. a base fluid) from being twice added to a single vessel 16. The protection circuit may thus prevent two tests from being run in the same vessel 16.

The testing apparatus 48 further includes a fluid injection system 50. The fluid injection system 50 may include a plurality of pumps, here two pumps 52, 54 being shown. During pump operation, each of the pumps may aspirate from a corresponding one of a like plurality of fluid containers 60, 62 for the first 180 degrees of rotation and will then dispense the aspirated fluid through a corresponding one of a like plurality of probes 64, 66 and into the reaction vessel 16 for the remaining 180 degrees of rotation. The pumps may aspirate fluid such as liquid acid and base solutions from respective ones of the containers 60, 62 and dispense the fluid through the probes 60, 62 (FIG. 1). The probes 60, 62 may be provided as uninterrupted tubes which allow the fluid to contact only the inside diameter of the tube with no transitions and only slight diametric variations. The probes 60, 62 may be coupled to like ones of the probes 30 (FIG. 1) which are preferably disposed such that the probes 30 provide fluid substantially into the center of the reaction vessel 16.

The pumps 52, 54 may be provided as fixed stroke pumps which deliver on the order of 300 microliter (ul) of fluid per stroke. Such pumps may be provided, for example, as the type described in U.S. Pat. No. 4,539,854 and U.S. Ser. No. 665,196 (Filed Mar. 4, 1991), both assigned to the assignee of the present invention and incorporated herein by reference. Alternatively any type of pump well known to those of ordinary skill in the art may also of course be used.

Each of the pumps 52, 54 may be coupled to and driven by a corresponding motor 56, 57 which may be provided for example as a stepper motors. The speed at which the motors 56, 57 operates may be user programmable via a controller 68 and thus an operator may select an appropriate speed at which to operate each of the motors 56, 57 and consequently the pumps 52, 54. The controller may be provided for example as a processor and may also be used to provide a preselected time delay between the acid dispense and base dispense operations.

The PMT assemblies 14a', 14b' are coupled to respective processors 70a, 70b which utilize the luminescence to provide constituent concentration information as is known in the art for single PMT systems.

Figure 4A:
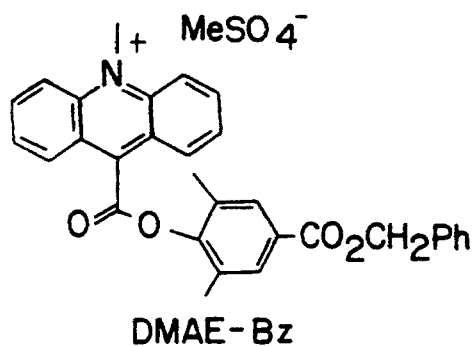
FIGS. 4A–4N illustrate the structures of representative acridinium esters, ABAC, and LBAC's.
Figure 4B:
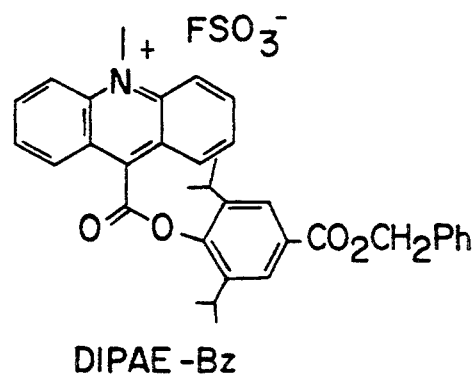
Figure 4C:
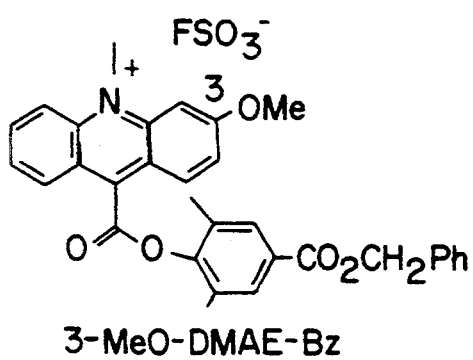
Figure 4D:
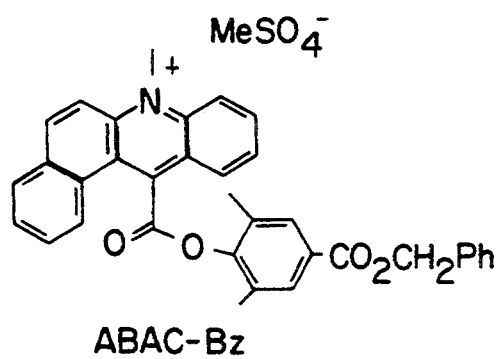
Figure 4E:
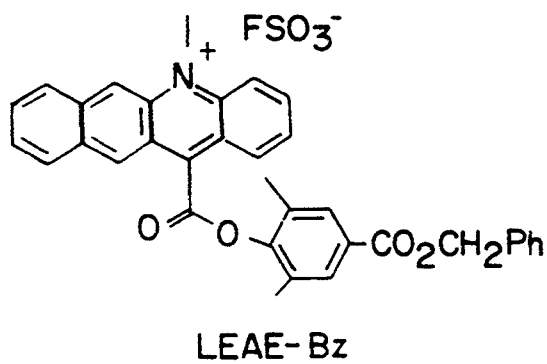
Figure 4F:
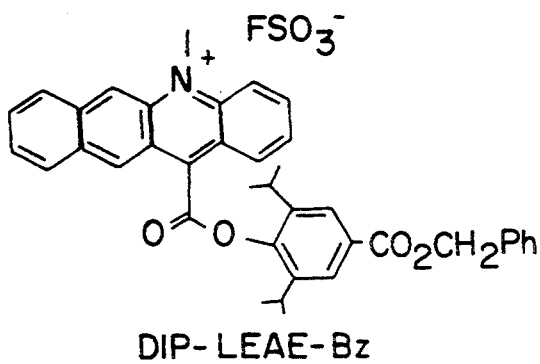
Figure 4G:
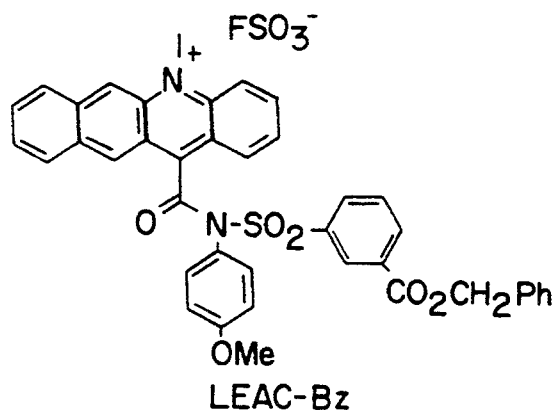
Figure 4H:
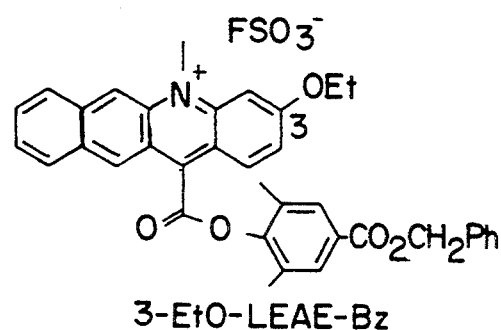
Figure 4I:
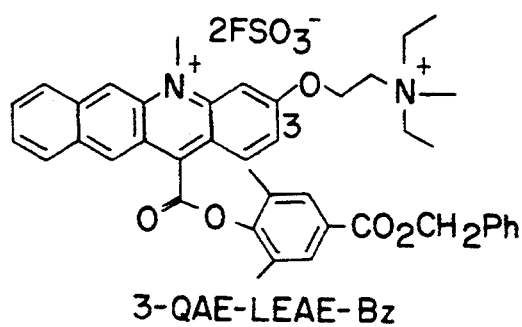
Figure 4J:
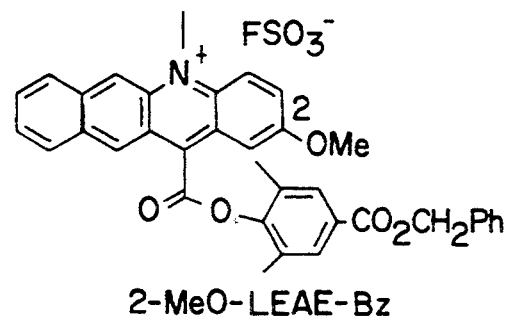
Figure 4K:
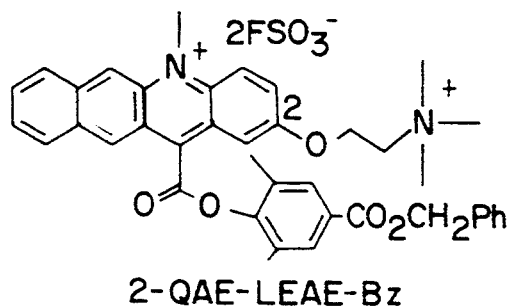
Figure 4L:
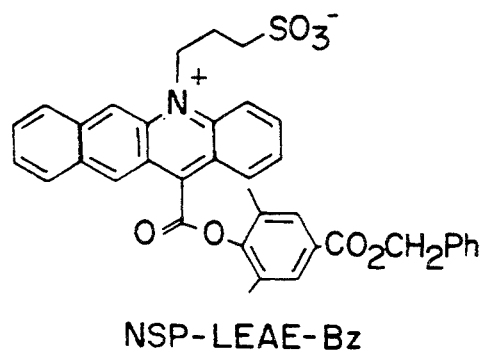
Figure 4M:
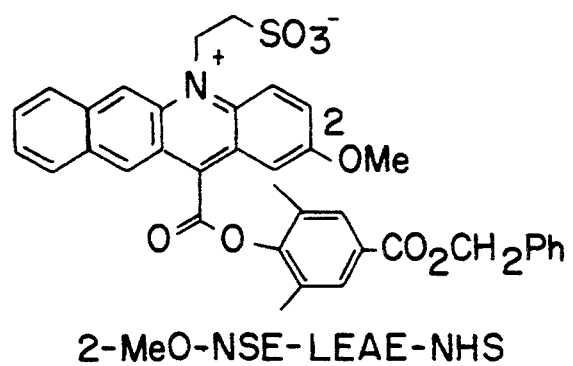
Figure 4N:
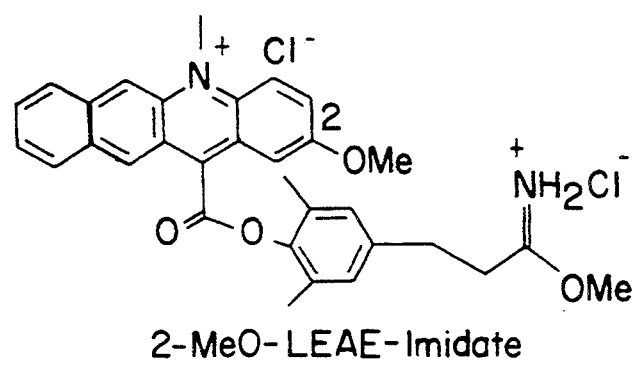

Representative compounds that may be reacted with a binding partner to form a conjugate or luminescent reagent and utilized in the practive of the present are shown in FIGS. 4A–4N.

PREPARATION OF CONJUGATES

In the chemiluminescent compounds of the present invention, preferably at the $R_6$ position, depending on which coupling moiety is selected, the AFAC label can be reacted directly with the specific binding partner, ligand, or hapten either in an aqueous or an organic medium.

It is understood that alternate positions of the chemiluminescent compound may have a coupling moiety to be reacted with a binding partner to form a conjugate.

The chemiluminescent labels can include an appropriate leaving group or an electrophilic functional group attached with a leaving group or functional groups which can be readily converted into such reactive groups, directly attached or connected via a spacer for attaching a substance to form a conjugate to be utilized in a test assay. An example of preparing the LEAE-anti-TSH conjugate is provided below.

Preparation of LEAE-Anti-TSH Conjugate A solution of a monoclonal anti-TSH antibody (2 mg, 0.013 umol) in 1.36 ml of 0.1M phosphate buffer, pH 8.0 was treated with a solution of LEAE-NHS (43 ug, 0.067 umole) in 240 ul of acetonitrile at room temperature for one hour.

The conjugation reaction was stopped by adding a solution of lysine (10 mg) in 0.5 ml of 0.1M phosphate buffer, pH 8. The LEAE-conjugated anti-TSH was purified by passing the reaction mixture through a Sephadex G-25 column (1×20 cm) packed and eluted with 10 mM Phosphate, pH 8. The elution was monitored at 280 nm with a ISCO UV detector. The desired conjugate was collected when the first void volume peak was eluted out.

Preparation of Oligonucleotide conjugate

A method for conjugating binding parties, haptens, or ligands of luminescent labels to polynucleotides is described in EP-A 0 537 994 (priority U.S. Ser. No. 775,399, filed Oct. 16, 1991, now abandoned), which is commonly assigned and incorporated herein by reference.

LIGHT EMISSION SPECTRA

The light emission spectra of LBAC's and the reference acridinium esters were determined by a Fast Spectral Scanning System (FSSS) of Photo Research (a division of Kollmorgen Corp) of Burbank, Calif., U.S.A. The experiment was carried out in a dark room. Each sample was dissolved in HPLC grade acetonitrile at the concentration of 1 mg/ml or higher and diluted with the same solvent to obtain the sample solution in the concentration specified. A typical determination utilized 10 to 100 ug of each compound, with the exception of the angular benz[a]acridinium ester (2 mg), separately or mixed together in 0.5 ml acetonitrile contained in 13×100 mm borosilicate test tube. The tube was placed on a tube rack raised to a proper height. The FSSS optical head was placed in front of the tube at close distance and with its lense focused on the liquid in the tube. The sample solution was first treated with 0.35 ml of the Flashing Reagent #1 (Ciba Corning Diagnostics) containing 0.1N $HNO_3$ and 0.1% $H_2O_2$. The room was then darkened, and 0.35 ml of the Flashing Reagent #2 (Ciba Corning Diagnostics) containing 0.25N NaOH and 0.2% ARQUAD was added to the reaction mixture immediately, see U.S. Pat. No. 4,927,769 which is commonly assigned and incorporated herein by reference. The light which was generated instantaneously following the addition of the Reagent #2 was recorded by FSSS for 4 seconds except for 2-MeO-LEAE-Imidate which was recorded for 30 seconds starting from split second before the Reagent #2 was added. The results of the various determinations are summarized in Table I.

TABLE I

| Compound | Quantity | Emission Max ~(nm) | Range* (nm) |
|---|---|---|---|
| 1. DMAE—Bz | 20 ug | 426–428 | 410–510 |
| 2. 3-MeO—DMAE—Bz | 50 ug | 422 | 395–520 |
| 3. DIPAE—Bz | 20 ug | 426 | 405–520 |
| 4. ABAC^ | 2 mg | 436–440 | 410–530 |
| 5. LEAE—Bz | 50 ug | 520–524 | 490–670 |
| 6. DIP—LEAE—Bz | 50 ug | 520 | 485–670 |
| 7. 2-MeO—LEAE—Bz | 30 ug | 550 | 510–700 |
| 8. 3-EtO—LEAE—Bz | 50 ug | 508 | 470–660 |
| 9. 3-QAE—LEAE—Bz | 100 ug | 544 | 470–680 |
| 10. 2-QAE—LEAE—NHS | 70 ug | 550 | 510–700 |

TABLE I-continued

| Compound | Quantity | Emission Max ~(nm) | Range* (nm) |
|---|---|---|---|
| 11. LEAC—Bz | 50 ug | 520 | 485–670 |
| 12. NSP—LEAE—Bz | 15 ug | 516 | 482–655 |
| 13. 2-MeO—NSE—LEAE—NHS | 50 ug | 546 | 500–700 |
| 14. 2-MeO—LEAE—Imidate | 100 ug | 550 | 500–710 |

~The emission maximum for each compound could vary by 0–4 nm between different determinations.
*Range is set for spectral region with signal intensity of above 5% of peak height.
^The ABAC is (4-Benzyloxycarbonyl-2,6-dimethyl)phenyl 5-methyl-benz[a]acridinium-12-carboxylate methosulfate.

Recorded emission spectra are shown in FIGS. 2A–2E, 3A–3J, and 4A–4D. FIGS. 2A–2E and 3A–3J show individual emission spectra of chemiluminescent compounds including an acridinium ring system and compounds including a benzacridinium ring system. The difference of the emission maxima between acridinium esters and LBAC's were found to range between 80–128 nm, while that between acridinium esters and the ABAC was about 8–14 nm. As shown in FIGS. 4A–4D, when the acridinium esters and LBAC's were mixed in a tube and flashed simultaneously, the resulting combined emission spectra showed the ideal summed up spectral profile, indicative of the non-interfering nature of these two groups of chemiluminescent emission signals. It is understood that these data may vary depending on the instrumentation utilized and the components of the instrumentation, particularly the filters. The major portions of the original constituting spectra which remained unchanged were indeed non-overlapping. These important physical characteristics fulfill the prerequisite for two or more subclasses of chemiluminescent compounds to be utilized in test assays for detecting and/or quantitating at least two substances in a test sample, and particulary to multianalyte clinical diagnostic assays. In the preferred method a benzacridinium compound is utilized as one component of the assay method and more specifically an N-alkylated benzacridinium compound.

As noted above, a luminometer for detecting and/or quantitating at least two chemiluminescent emission spectra is described in U.S. Ser. No. 07/665,196, filed Mar. 4, 1991.

LIGHT EMITTING EFFICIENCY

Figure 5A:
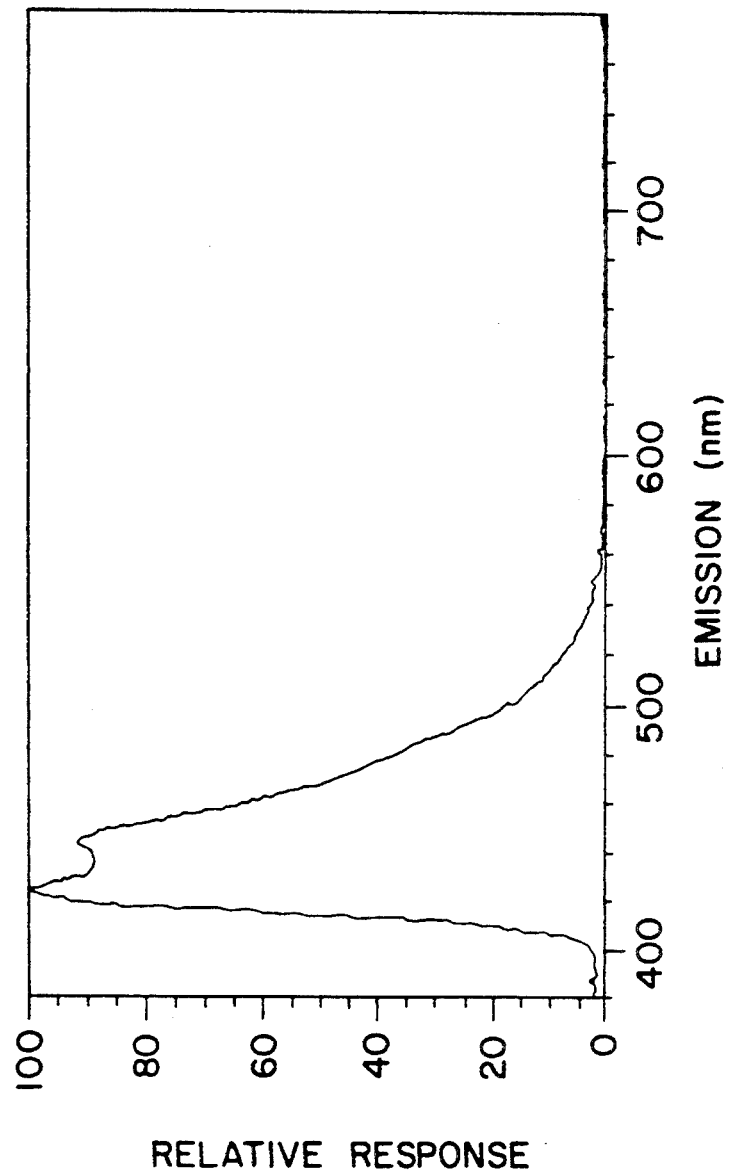
Figure 5B:
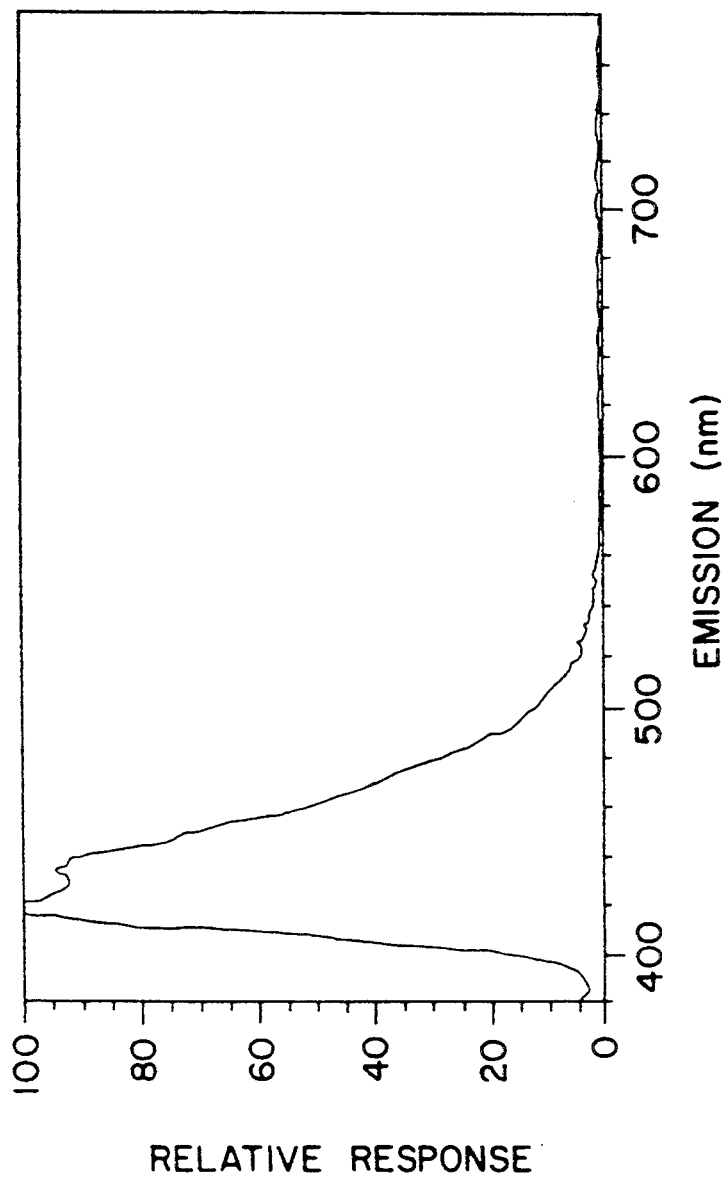
Figure 5E:
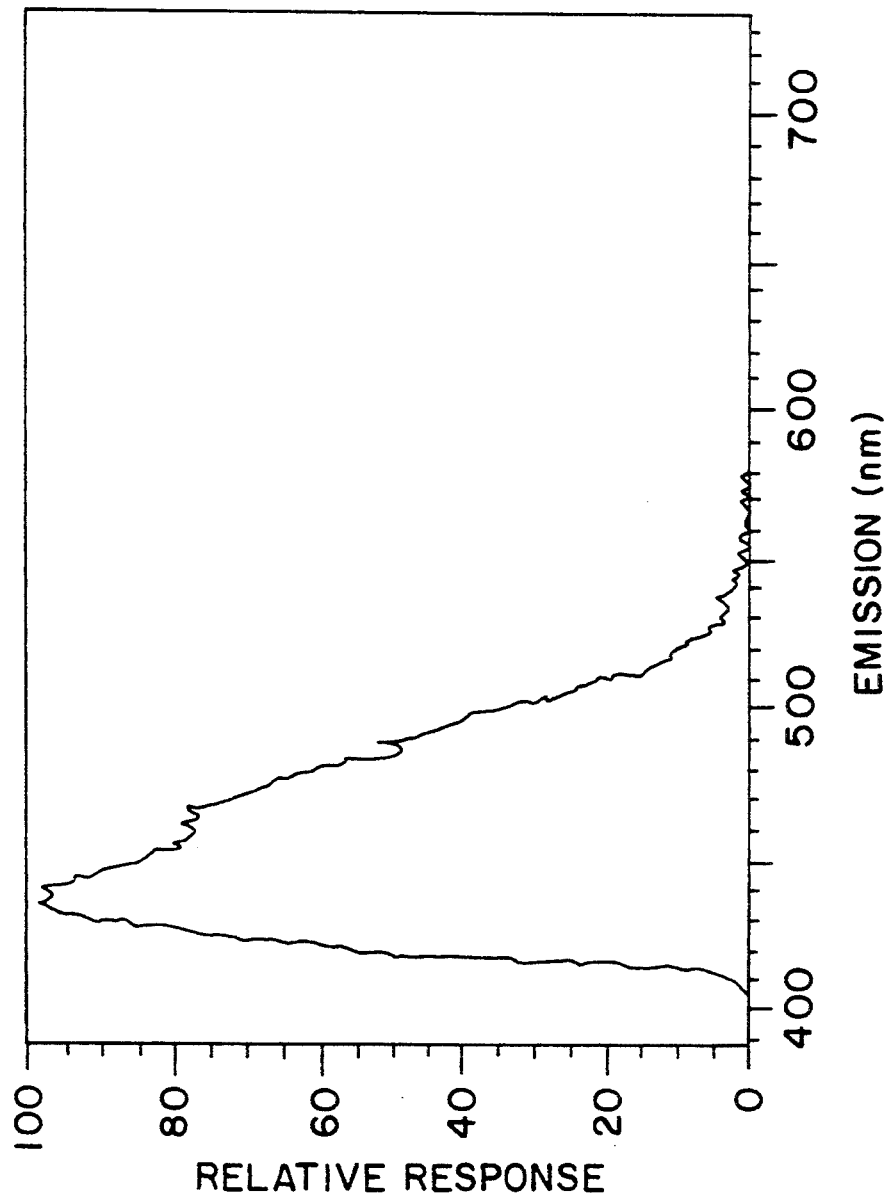
Figure 6A:
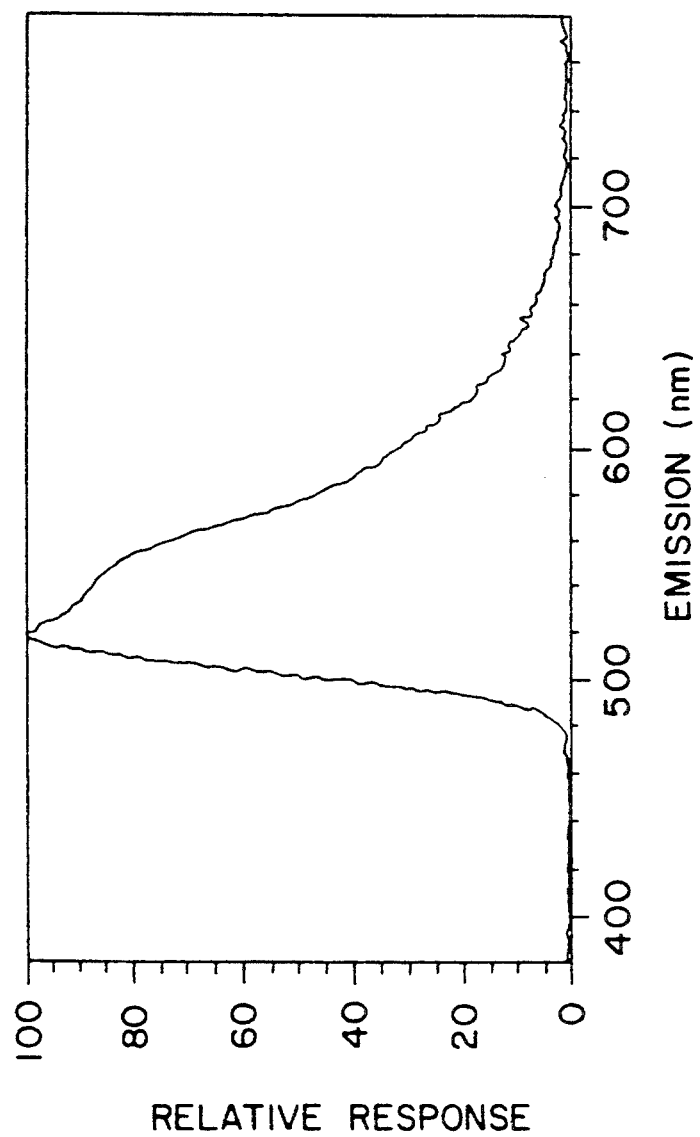
Figure 6D:
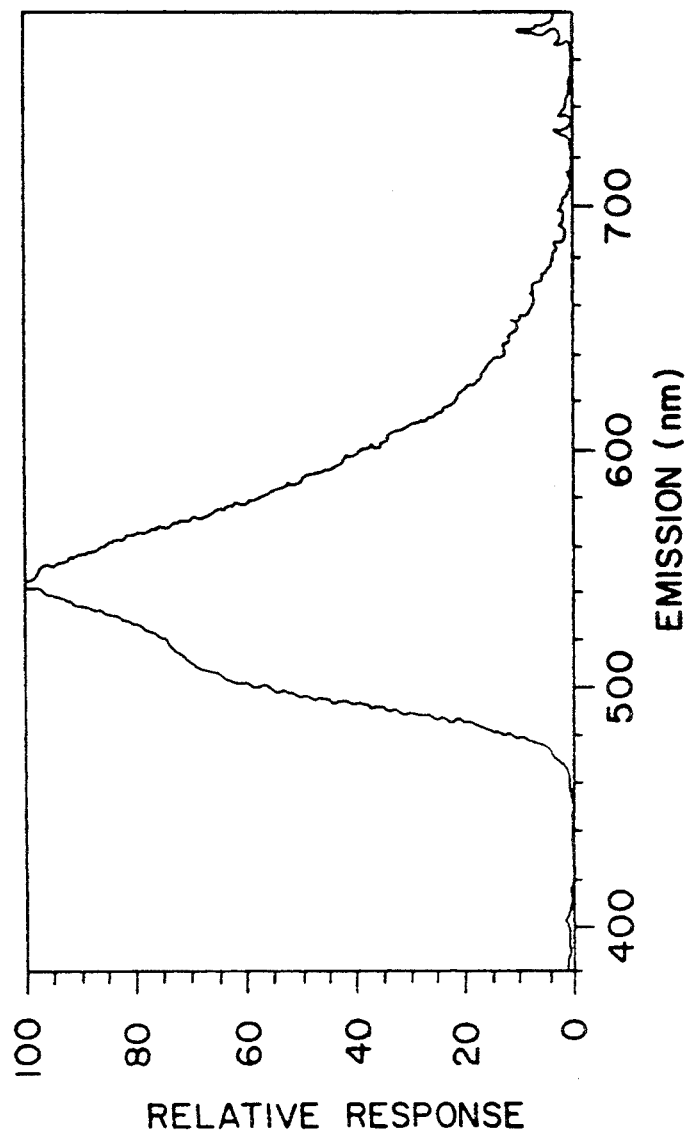
Figure 6E:
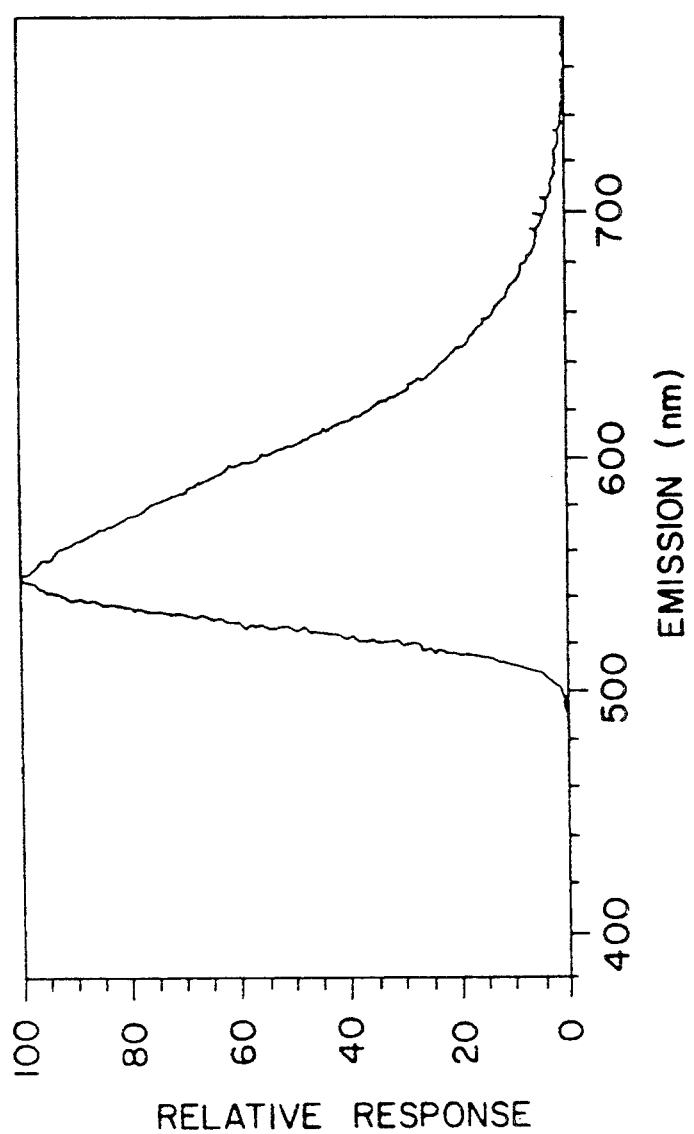
Figure 6F:
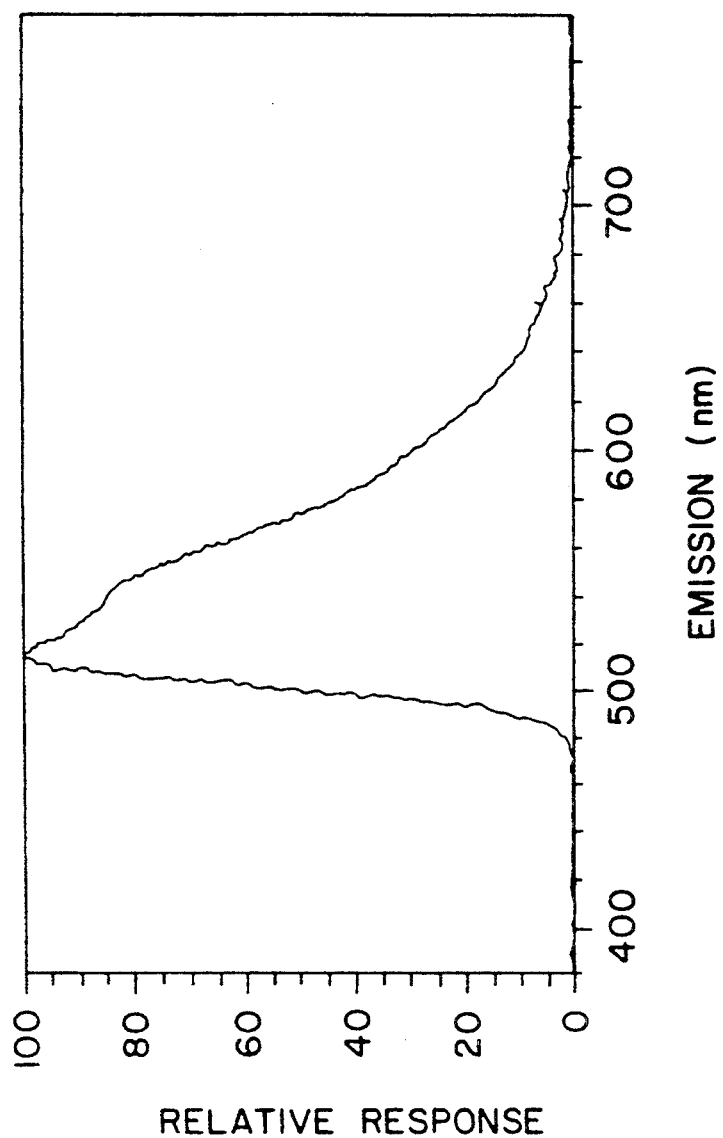
Figure 6G:
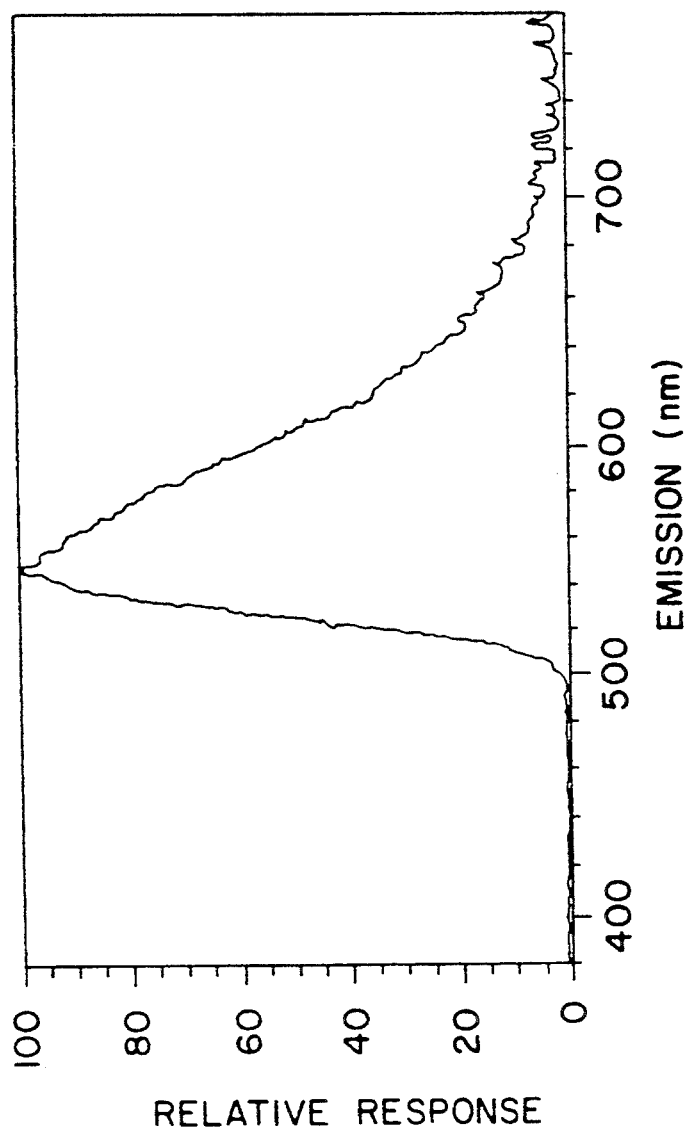
Figure 6H:
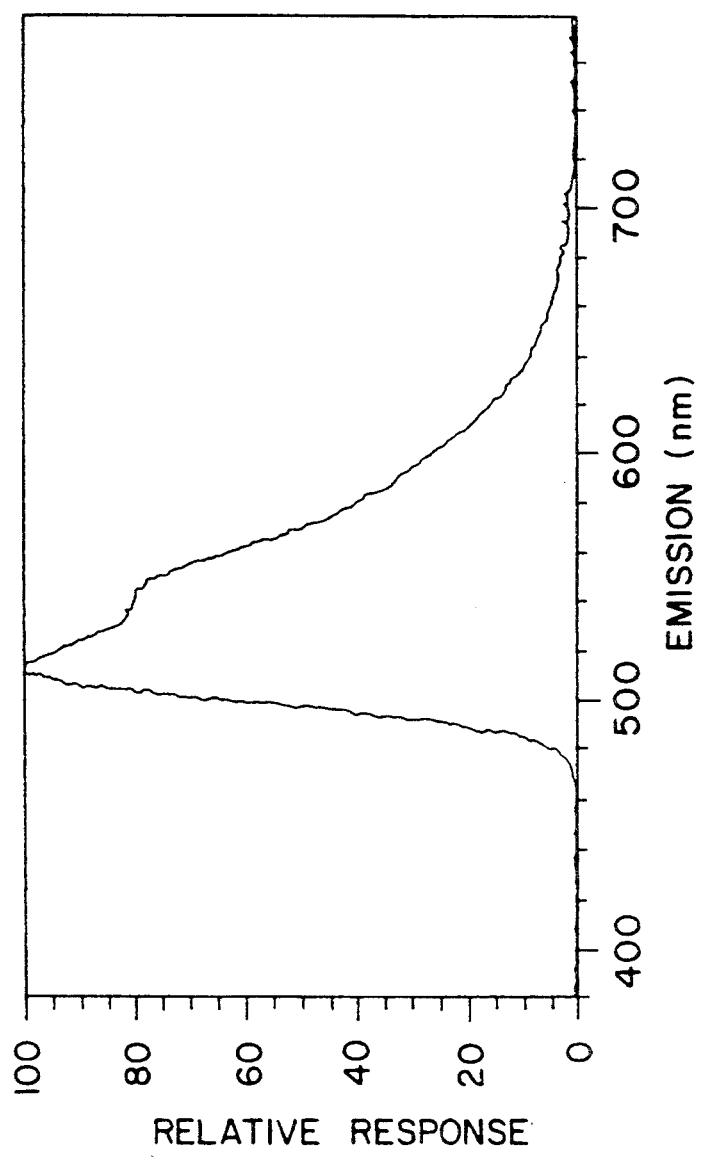
Figure 6I:
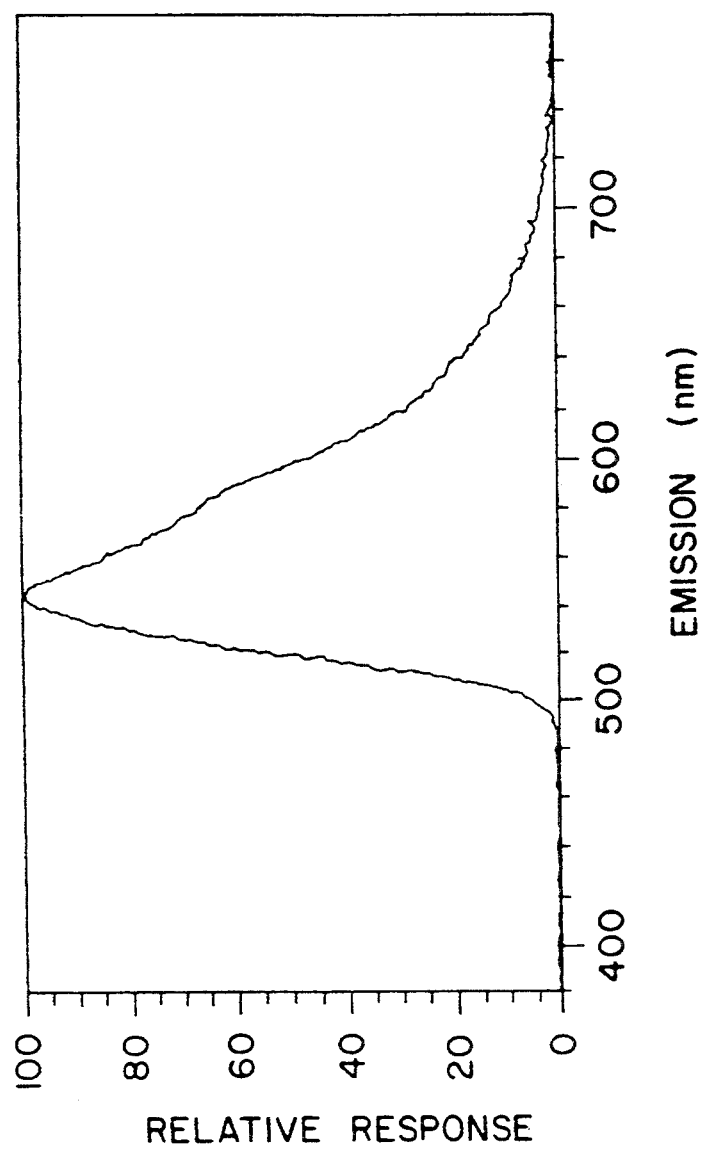
Figure 6J:
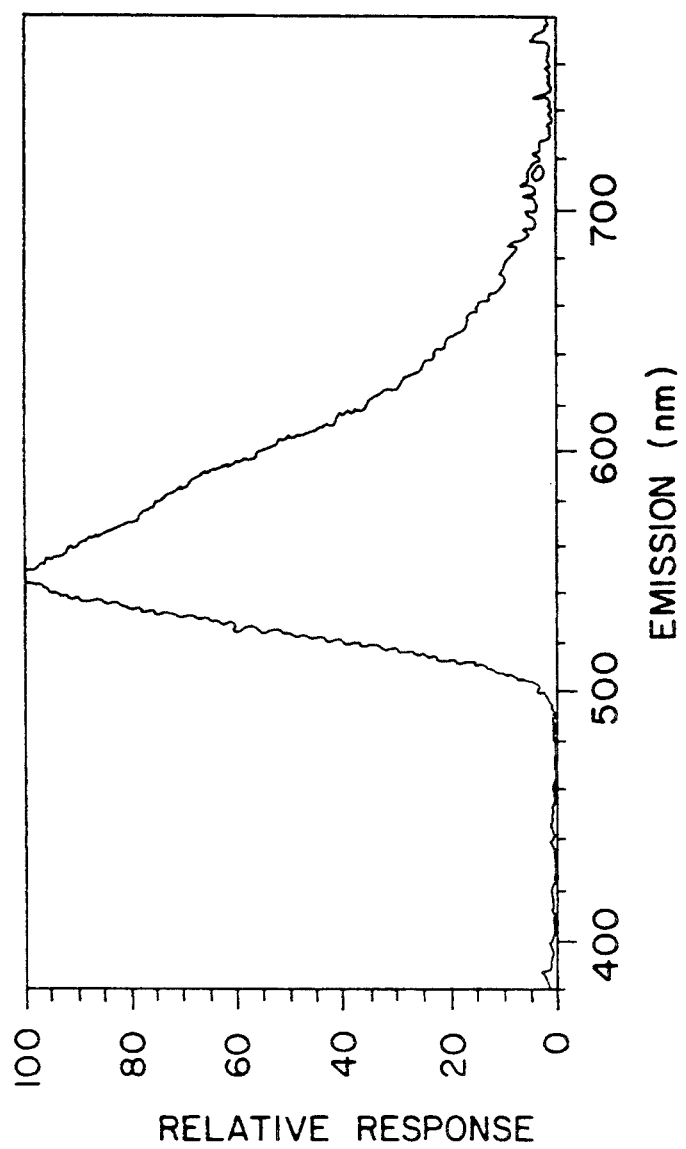
Figure 7A:
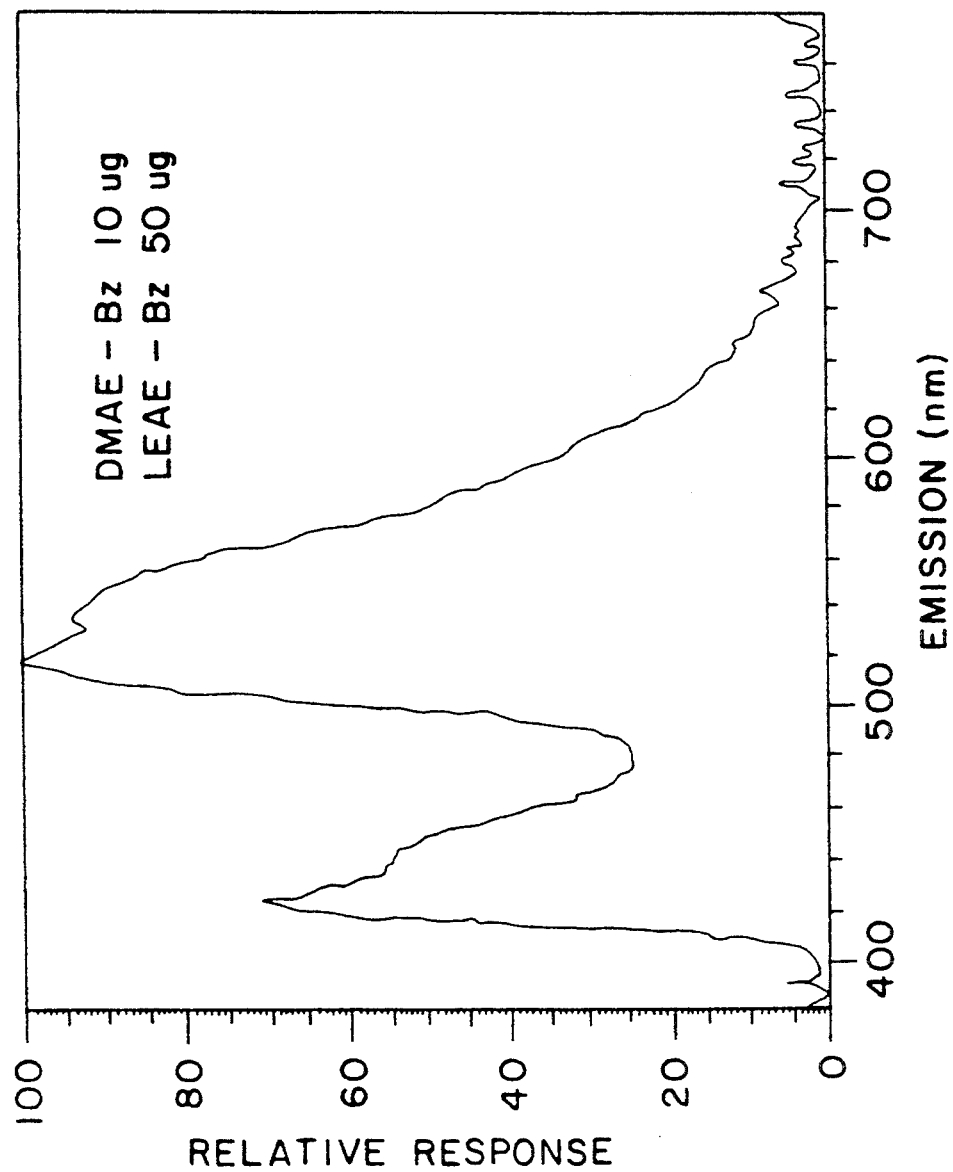
FIGS. 7A–7D illustrate emission spectra of mixed acridinium esters and LBAC.
Figure 7B:
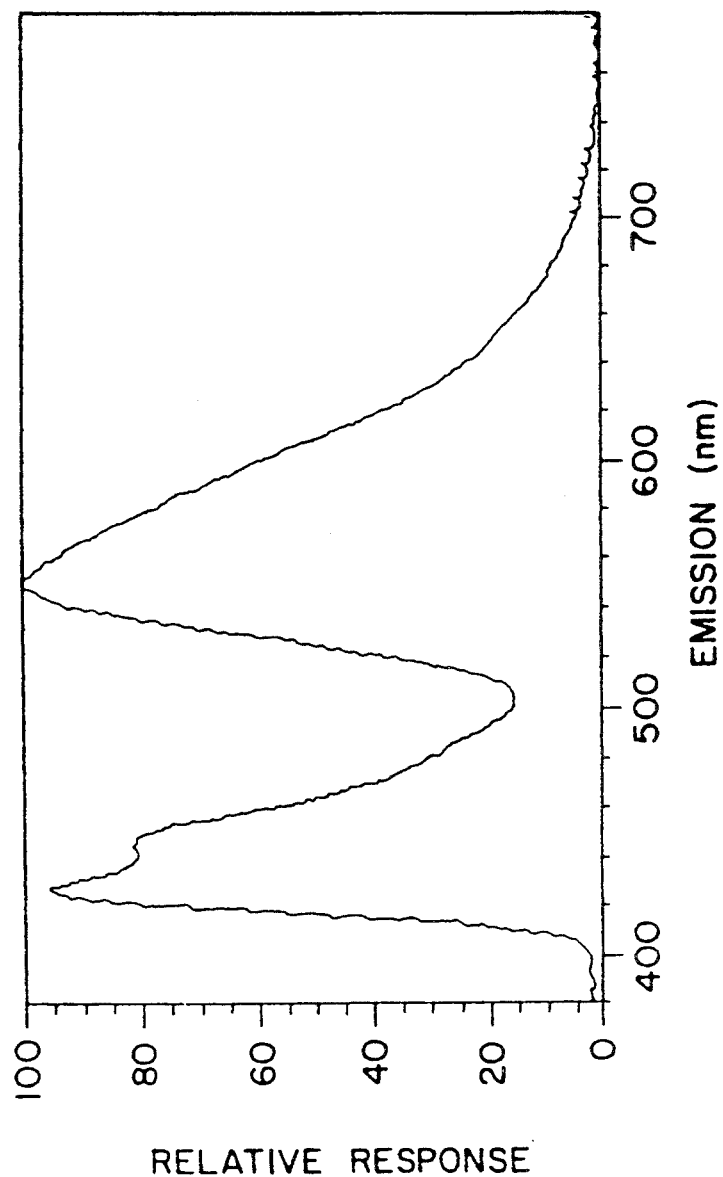
Figure 7C:
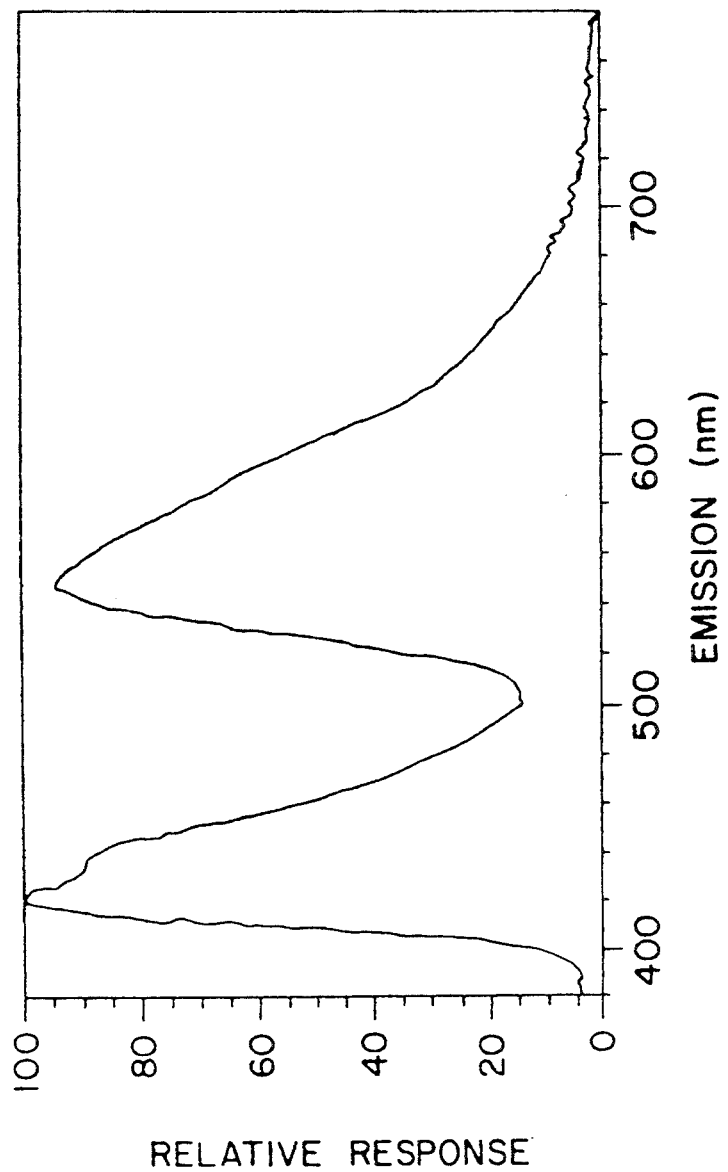
Figure 7D:
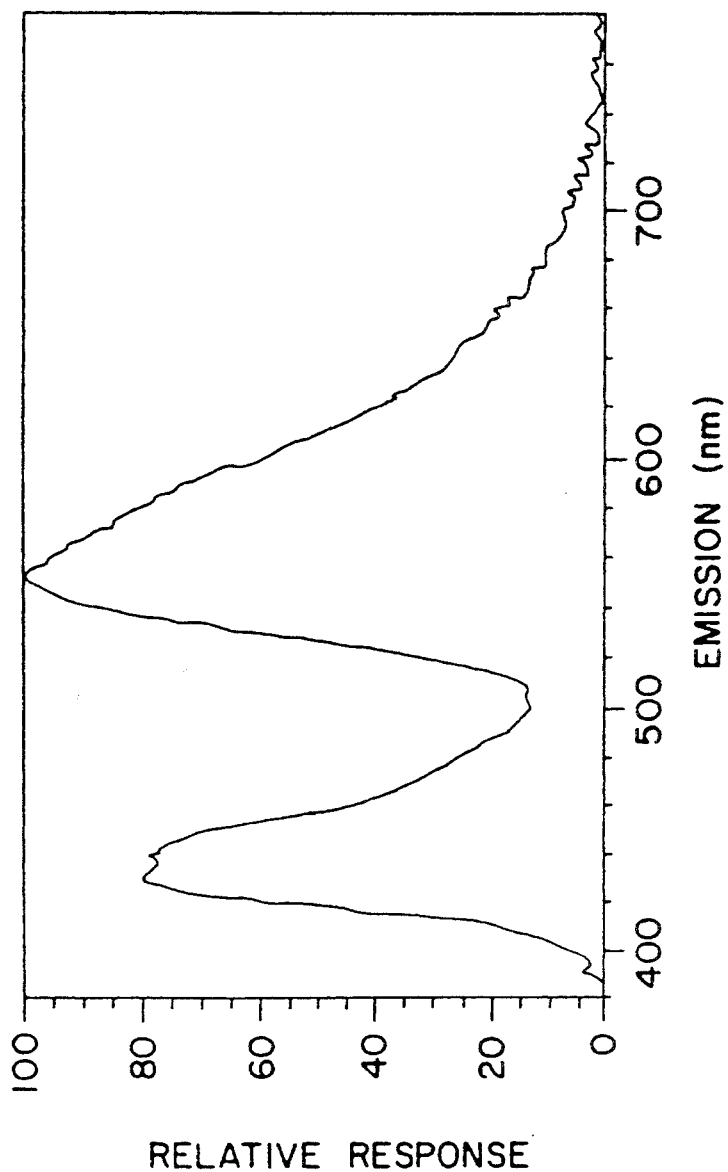
Figure 8A:
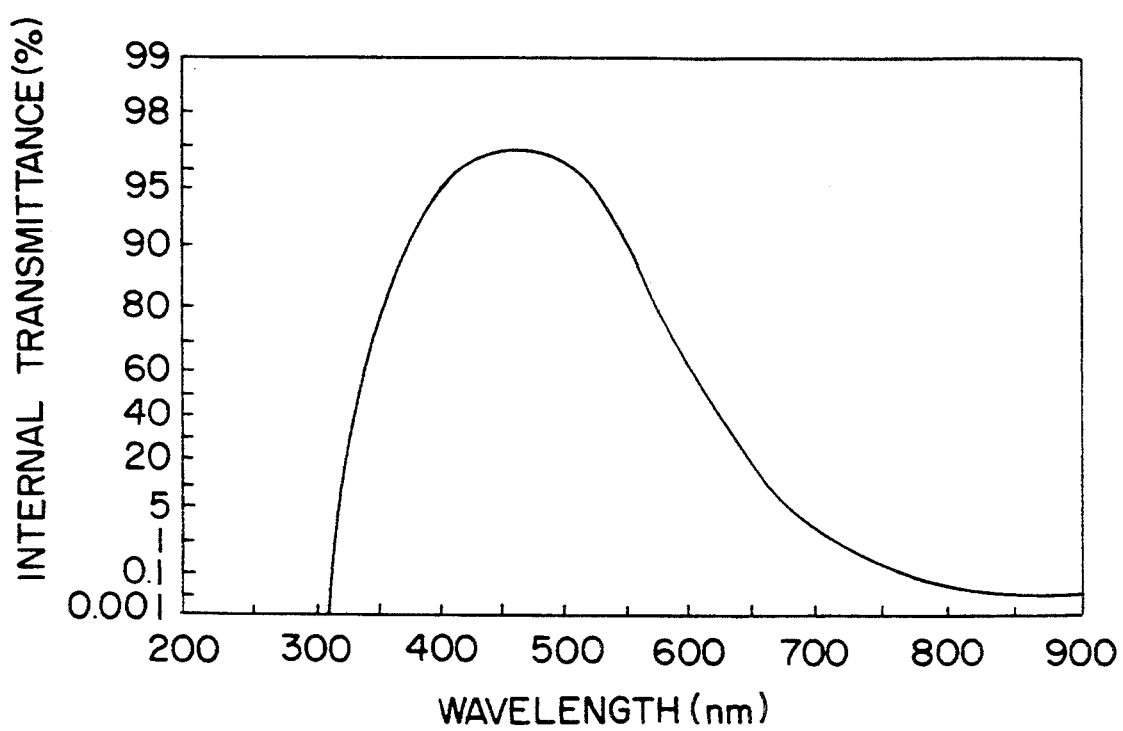
FIGS. 8A–8E illustrate transmittance curves of various optical filters.
Figure 8B:
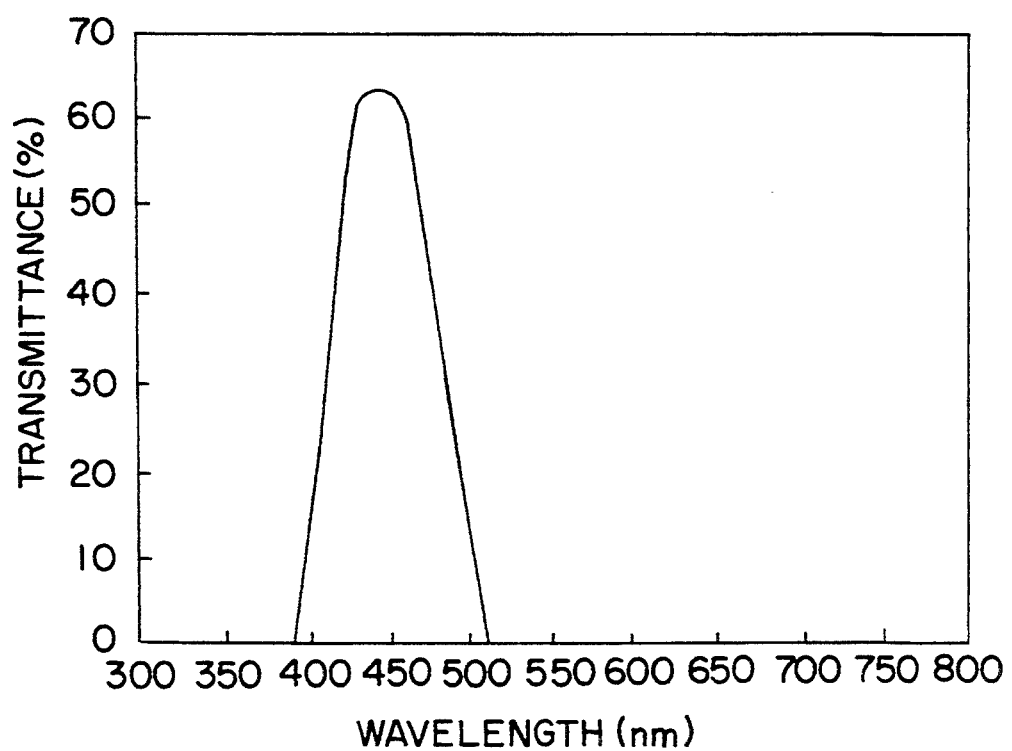
Figure 8C:
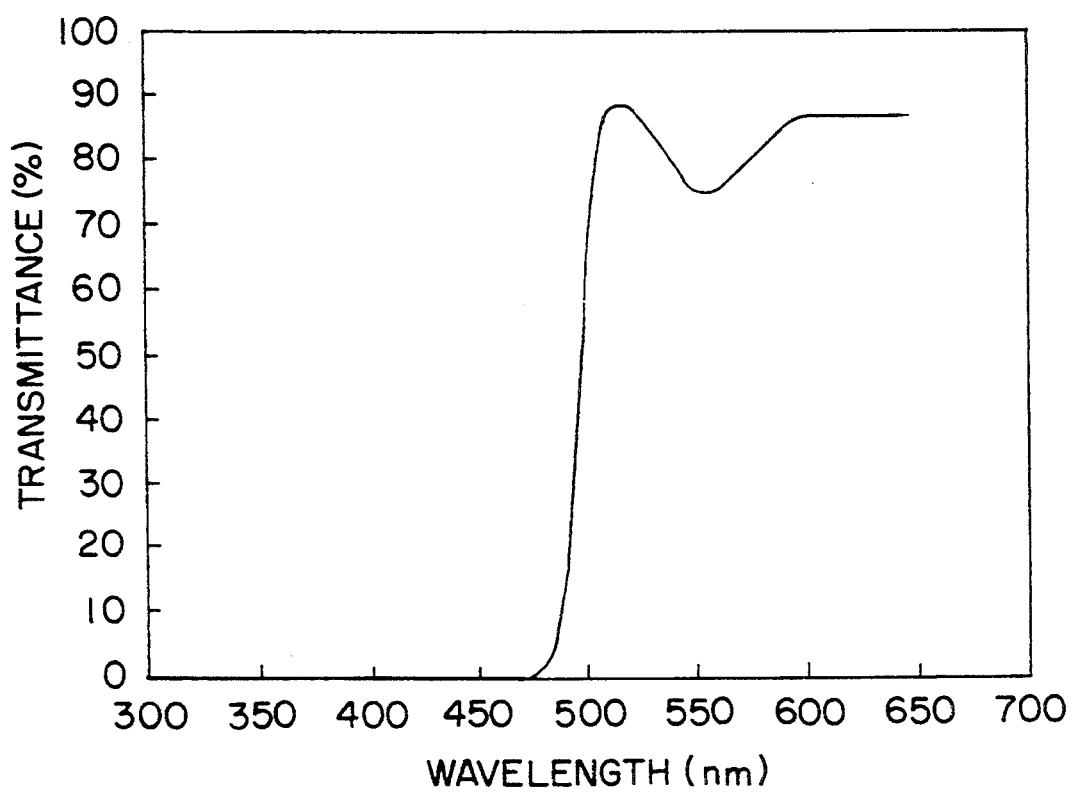
Figure 8D:
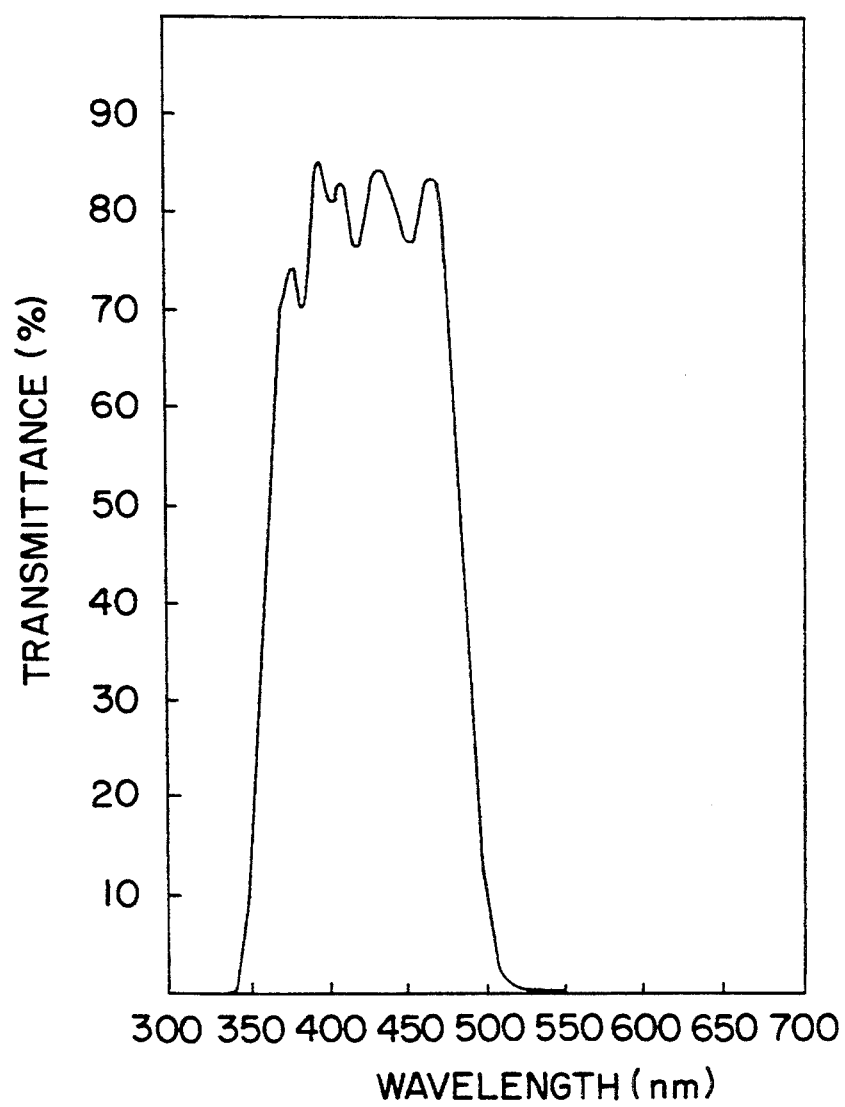
Figure 8E:
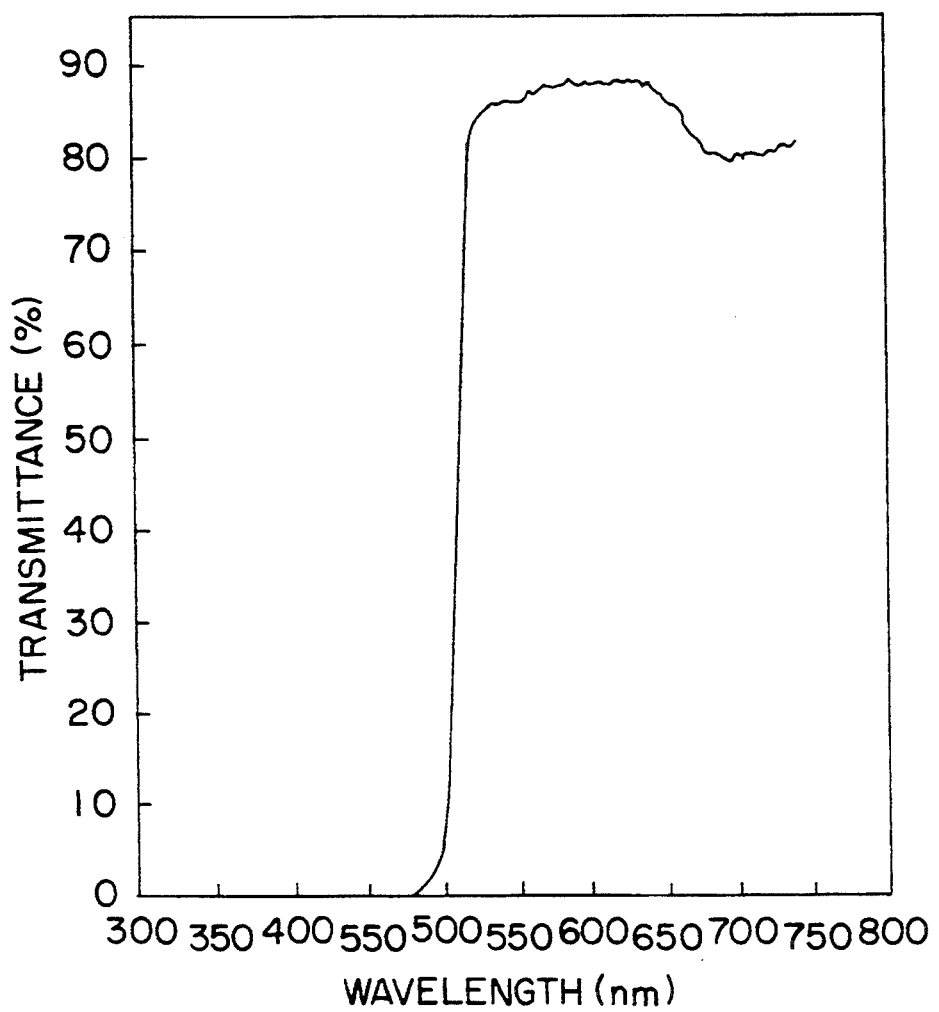

The light emitting efficiency of LBAC's, ABAC, and DMAE-Bz was determined on a Berthold luminometer (MLA-I) (Ciba Corning Diagnostics Corp.) fitted with a BG-38 filter with wavelength transmission range of about 320 to 650 nm at transmission efficiency of 20 to 97%. (FIG. 5, Panel A). Alternate filters may be incorporated in luminometers to expand the range of transmission efficiency.

Each sample was prepared in acetonitrile solution at 1 mg/ml, serially diluted to 10 ug/ml in acetonitrile and further on to 1 ng/ml, 0.1 ng/ml and 0.01 ng/ml in 10 mM phosphate buffer iwht 0.15M NaCl, 0.1% BSA. 0.05% $NAN_3$, pH8.

To determine the light emitting efficiency, 25 ul of blank (the buffer matrix) or each sample were flashed by injecting 0.35 ml each of the Flashing Reagent #1 and #2 sequentially. Light emission was integrated for 2 seconds and results as means of duplicate determination are given in Table II.

TABLE II

| Compound (counter ion) | Molecular Weight | Total Counts (RLU's)/2 sec amount flashed (pg) | | | RLU's/mol* (1 × E20) |
|---|---|---|---|---|---|
| | | 0.25 pg | 2.5 pg | 25.0 pg | |
| DMAE—Bz (CH₃SO₄⁻) | 587 | 76,477 | 769,477 | 6,786,57 | 1.8 |
| DIPAE—Bz (FSO₃⁻) | 631 | 82,115 | 845,660 | 6,041,380 | 2.1 |
| 3-MeO—DMAE—Bz (FSO₃⁻) | 605 | — | 54,760 | 523,380 | 0.13 |
| ABAC^ (CH₃SO₄⁻) | 613 | — | 23,600 | 143,400 | 0.058 |
| LEAE—Bz (FSO₃⁻) | 625 | 105,857 | 1,037,943 | 9,037,063 | 2.6 |
| DIP—LEAE—Bz (FSO₃⁻) | 681 | 29,930 | 240,610 | 2,413,320 | 0.66 |
| LEAC—Bz (FSO₃⁻) | 766 | 79,873 | 767,553 | 6,312,163 | 2.4 |
| 3-EtO—LEAE—Bz (FSO₃⁻) | 669 | 93,635 | 883,785 | 6,364,935 | 2.4 |
| 3-QAE—LEAE—Bz (FSO₃⁻) | 854 | 16,765 | 107,540 | 1,005,855 | 0.37 |
| 2-MeO—LEAE—Bz (FSO₃⁻) | 655 | 27,810 | 223,995 | 2,140,890 | 0.59 |
| 2-QAE—LEAE—NHS (FSO₃⁻) | 854 | ND~ | ND~ | ND~ | ND~ |
| NSP—LEAE—Bz | 633 | 22,715 | 212,485 | 2,250,520 | 0.54 |
| 2-MeO—NSE—LEAE—NHS | 646 | 14,853 | 145,403 | 1,503,100 | 0.38 |
| 2-MeO—LEAE—Imidate (2 Cl~) | 578 | ND~ | ND~ | ND~ | ND~ |

*counts/mol calculated from quantity of 2.5 pg.
^The ABAC is (4-Benzyloxycarbonyl-2,6-dimethyl)phenyl 5-methyl-benz[a]acridinium-12-carboxylate methosulfate.
~ND = not determined prior to the establishment of final purity of the compound.

From the data shown in Table II, the light emitting efficiency of the LBAC's was comparable to that of DMAE-Bz within the range of 0.21 to 1.39 fold, depending on the substitutents on the benzacridinium nucleus and the phenoxy group. It should be noted these determinations were based on 2-second signal collection and have not taken into account the flashing kinetics of the individual compounds, e.g. some compounds may take greater thatn 2 seconds to release most of their signals, the sensitivity of the photomultiplying tube, and the transmission efficiency of the optical filter(s) at different points of the spectral range. These findings, however, were totally unexpected in view of the much lower light emitting efficiency of the isomeric ABAC. This level of light emitting efficiency renders LEAC's useful in sensitive binding assays, including multi-analyte assays.

KINETIC STUDY ON LIGHT EMISSION

Due to the electronic and/or steric effects of different substituents on the phenoxy moiety, the acridinium and benzacridinium nucleus, it was anticipated that not all the DMAE analogs, ABAC and LEAC's would have the same flashing rates under identical conditions. In other words, within 2 seconds of signal collection time different compounds were expected to release different percentages of total releasable signals. A time course study over a period of up to 10 seconds was conducted to determine these percentages, by flashing the compounds and normalizing all the signals collected for different lengths of time to that of 10 seconds. The results are summarized in Table III.

TABLE III

| | Percent signal released over different lengths of time | | | | | |
|---|---|---|---|---|---|---|
| Compounds | 10.0 s | 6.0 s | 4.0 s | 2.0 s | 1.0 s | 0.5 s |
| DMAE—Bz | 100% | 99% | 96% | 80% | 48% | 10% |
| DIPAE—Bz | 100% | 98% | 97% | 89% | 64% | 14% |
| 3-MeO—DMAE—Bz | 100% | 80% | 70% | 57% | 49% | 26% |
| ABAC^ | 100% | 89% | 73% | 52% | 20% | 3% |
| LEAE—Bz | 100% | 98% | 97% | 88% | 71% | 27% |
| DIP—LEAE—Bz | 100% | 80% | 67% | 47% | 26% | 4% |
| LEAC—Bz | 100% | 102% | 98% | 93% | 82% | 73% |
| 3-EtO—LEAE—Bz | 100% | 95% | 93% | 85% | 78% | 45% |
| 3-QAE—LEAE—Bz | 100% | 91% | 88% | 84% | 75% | 34% |
| 2-MeO—LEAE—Bz | 100% | 92% | 83% | 65% | 42% | 16% |
| 2-QAE—LEAE—NHS | 100% | 88% | 76% | 59% | 37% | 9% |
| NSP—LEAE—Bz | 100% | 95% | 96% | 91% | 72% | 14% |
| 2-MeO—NSE—LEAE—NHS | 100% | 96% | 90% | 79% | 58% | 22% |
| 2-MeO—LEAE—Imidate | 100% | 76% | 59% | 40% | 23% | 6% |

^The ABAC is (4-Benzyloxycarbonyl-2,6-dimethyl)phenyl 5-methyl-benz[a]acridinium-12-carboxylate methosulfate.

As shown by the data of TABLE III, particularly at the 0.5 and 1 second intervals, the flashing kinetics varied widely for different DMAE analogs, ABAC and LEAC's. These data on release percentages should be utilized in comparing the light emission efficiency of the compounds for developing various assay utilizing the chemiluminescent compounds.

MUTUALLY NON-INTERFERING LIGHT EMISSION

Beside exhibiting discernable mutually non-interfering nature of their light emission spectra as mentioned above, DMAE and LEAE in the form of protein conjugates also demonstrated no mutual interactions in their light emissions during flashing as shown by no decrease or increase of the combined Relative Light Units (RLU) registered.

The testing was carried out as follows:

DMAE-anti-TSH and LEAE-anti-TSH were diluted in 10 mM phosphate buffer with 0.15M NaCl, 0.1% BSA, 0.05% NaN$_3$, pH 8 at two concentrations, such that 25 ul of the solutions would give about 200,000 and 1,000,000 RLU's, respectively, when they were flashed in the same manner on the Berthold luminometer equipped as described above. The light emission of each sample (25 ul) was measured separately and then the same volume of each were combined and measured again. In single sample determinations, an additional equal volume of the buffer was added to maintain the same sample volume as in the combined sample determinations. Results of the testing are summarized in Table IV.

TABLE IV

| Single sample determination* (RLU) | | Combined sample determination* (RUL) | |
|---|---|---|---|
| DMAE-anti-TSH | LEAE-anti-TSH | Theoretical | Found (%) |
| 860,617 | 1,017,200 | 1,877,817 | 1,835,350 (98%) |
| 173,200 | 191,820 | 365,029 | 362,293 (99%) |

*Each value was the mean of triplicate determinations. (RLU — Relative light units)

The results in Table IV show that the two tracers of different emission spectra were absolutely non-interfering between each other in their light emission. This characteristic further ensures their utility in multi-analyte binding assays. The LEAE of the preferred method is a N-alkylated benzacridinium compound.

STABILITY of CONJUGATED LBAC'S

LBAC-Anti-TSH conjugates were prepared and tested for their stability in aqueous media. DMAE-anti-TSH conjugate was also tested side by side. The retention of chemiluminescent activity as a function of temperature at various pH's (using citrate-phosphate buffer containing 0.1% BSA) was monitored over 7 day period. Proper concentrations of the above conjugates (0.8–1.4×10$^6$ RLU's/25 ul) were placed in two sets of different buffers (pH 7.4, 8.0, 8.5, and 9.0). One set was kept at 4°–8° C. as a control, while the other was subjected to 37° C. The buffered samples (25 ul) were flashed periodically as described above. The results are summarized in Table V.

TABLE V

| pH | Compds^ | Relative Stability* of Conjugates | | | |
|---|---|---|---|---|---|
| | | 1 day | 3 days | 5 days | 7 days |
| 7.4 | I | 93% | 98% | 91% | 95% |
| | II | 66% | 56% | 51% | 44% |
| | III | 67% | 78% | 77% | 80% |
| | IV | 89% | 94% | 101% | 96% |
| | V | | 66% | | 46% |
| 8.0 | I | 99% | 104% | 96% | 98% |
| | II | 106% | 106% | 80% | 83% |
| | III | 79% | 69% | 68% | 71% |
| | IV | 102% | 114% | 140% | 138% |
| | V | | 45% | | 13% |
| 8.5 | I | 92% | 102% | 89% | 81% |
| | II | 111% | 97% | 110% | 82% |
| | III | 81% | 76% | 78% | 86% |
| | IV | 134% | 142% | 150% | 156% |
| 9.0 | I | 90% | 95% | 70% | 71% |
| | III | 94% | 68% | 51% | 71% |
| | IV | 133% | 140% | 149% | 130% |

^Compounds I–V are DMAE-anti-TSH, LEAE-anti-TSH, 2-MeO—LEAE anti-TSH, 3-EtO—LEAE-anti-TSH, and Non-ortho-substituted AE-anti-TSH, respectively. The stability data for Non-ortho-substituted AE-anti-TSH were equivalent to that reported earlier in U.S. Pat. No. 4,745,181.

*Relative Stability is defined by expressing the percentage chemiluminescent activity of 37° C. samples relative to that of the corresponding 4–8° C. samples. For example, at pH 8, after 7 days of storage, the DMAE-anti-TSH and LEAE-anti-TSH 37° C. samples retained 87% and 83% acitivity, respectively, in comparison with the corresponding 4° C. samples, while the non-ortho-substituted acridinium ester retained only 13% activity in comparison with the corresponding 4° C. sample.

The stability study summarized in Table V demonstrates that the stabilizing effect of ortho-substitution on the phenoxy ring not only applies to the class of acridinium esters, it also benefits the LBAC's series to about the same extent with regard to maintaining their chemiluminescent activity in aqueous media at or near pH 8 under prolonged heat-stress conditions as required for commercial binding assay products. Listed in great contrast is the stability data of the non-ortho-substituted acridinium ester conjugate at pH 8. A non-ortho-substituted LEAC would likely also have poor stability in aqueous media.

Signal-to-Noise in Binding Assays

LEAE-anti-TSH was employed as tracer in a TSH assay. Performance was assessed by determining signal-to-noise (S/N) ratio. The performance of DMAE-antiTSH was also compared side by side. The assay was configured as follows:

100 microliters of either of the above conjugates was incubated for two hours at room temperature with 100 ul of a TSH standard (Ciba Corning Diagnostics Corp., Medfield, Mass.). Incubations were done separately with five standards containing either 0, 0.5, 1.0, 16 or 100 uIu/ml of TSH. A second incubation was then performed by adding 500 ul of MAGIC®magnetic particle immobilized with sheep anti-TSH (Ciba Corning Diagnostics Corp.) to the above mixture, then waiting for 30 minutes at room temperature.

A wash was done first by magnetically separating the particles from the solution, decanting the solution, then adding 500 ul of water, followed by another magnetic separation. The washed particles were resuspended in 100 ul of water. Flashing and counting were done according to the above-described procedures. The results are provided in Table VI using ratios of the counts with a TSH standard containing TSH versus the zero TSH standard.

TABLE VI

| Conjugate | S/N at various Standards | | | |
|---|---|---|---|---|
| | 0.4 uIu/ml | 1.0 uIu/ml | 16 uIu/ml | 100 uIu/ml |
| DMAE-anti-TSH | 10.0 | 20.9 | 202.3 | 669.4 |
| LEAE-anti-TSH | 5.4 | 8.4 | 87.4 | 282.6 |

The results given in Table VI indicate that LEAE conjugate can be utilized in an immunoassay format to provide a dose-response curve and, therefore, allows the development of useful assays.

DUAL-ANALYTE SIMULTANEOUS IMMUNOASSAY

Instrumentation

One embodiment of a Dual-PMT Luminometer (DPL) utilized to demonstrate the hardware of DPL includes at least two photo multiplyer tube (PMT) assemblies, an injection pump for Flashing Reagent #2, and a cube-shape light tight chamber designed for holding a disposable cuvette. At two opposite sides of the chamber, two cylindrical PMT tube assemblies are separately attached such that light of two different spectral ranges generated inside the cuvette can be individually registered by the PMT assemblies. The top of the cuvette-holding chamber is hinged to allow the cuvette to be manually inserted and removed. In addition, the top also has a fixed probe attached for the purpose of injecting the Flashing Reagent #2 into the cuvette. Within each PMT assembly an optical filter selected for particular spectral range, and is inserted between the cuvette and the PMT tube.

Alternate embodiments and configurations of DPLs may be designed for semi-automated and automated detection of two or more chemiluminescent compounds or conjugates in a test sample. A luminometer as a component on an automated analyzer is described in EP-A-0 502 638 noted above.

Essential to the discrimination or discernability of two or more emitted light spectra are the choices of a plurality of optical filters with proper wavelength cut-offs.

Filters of this type are widely available from commercial vendors and may be modified, i.e. by lamination or specifically manufactured to be incorporated in a PMT assembly for detection and/or quantitation of spectral signals of the conjugates. Careful selection of filters will enhance the ability to discern emission signals and with appropriate correction may allow multiple signals with the emission overlap to be discerned.

For the purpose of running a simultaneous LH/FSH dual-immunoassay as disclosed below, a long pass filter (P/N LL-500 of Corion, Holliston, Mass.) and a short pass filter (P/N P70–450 also of Corion) were chosen to match with the two different spectral ranges of light generated from a pair of tracers, LEAE-anti-LH and DMAE-anti-FSH, which were prepared in the same manner as described above for LEAE-anti-TSH and DMAE-antiTSH, respectively. The transmittance curves for the two filters are shown in FIG. 5, panels B and C. The choice of the optical filters should take into consideration the requirements on maximal signal transmittance and minimal signal cross-talk. Optical filters with more desirable transmittance profile and cut-off may be selected to maximize the transmission of light emitted from the tracers and/or to fit better with the emission spectral ranges of particular chemiluminescent compounds so as to improve the Percent Cross Talk (PCT) as described below. For example Corion's laminated CS550/CS600 filter (FIG. 5, panel D) was found to be a better replacement for filter P70–450 as the short pass filter matching with the long pass filter LL-500 for the determination of the pair of DMAE and LEAE tracers. Not only was the registered RLU's for DMAE tracer found to increase by more than 2 fold as a result of this filter's use, the Percentage Cross Talks, as shown in Table VII, were also greatly improved. Furthermore, as more LEAE derivatives with even longer emission maxima were developed, e.g. 2-MeO-LEAE, long pass filters such as LL-520 (FIG. 5 E) would be a better choice than filter LL-500 for enabling further reduction of the PCT.

For system controlling, which generally includes the basic functions of parameter setting, execution and registration of flashing, signal correction as described below as a function of filters used and the chemiluminescent compounds utilized, and data display, a personal computer unit containing proper software is utilized and connected to the DPL.

Percentage Cross-Talks (PCT's) Determination

As mentioned above the two optical filters installed in two separate PMT assemblies on the DPL were intended to gate the emitted lights of two different spectral ranges: the long pass filter is to match with the longer emission from LEAE tracer and the short pass filter with the shorter emission from DMAE tracer. However, as illustrated by FIGS. 6 and 7, because of the minor overlap between the transmittance curves and the emission spectra of the cross-matching pairs, light signals generated by one tracer can be picked up by the primary PMT intended for it but also in small percentage by the secondary PMT intended for the other tracer, and vice versa. That portion of signal of one tracer, that can be registered by the secondary PMT, must be quantitated separately in term of percentage for each tracer prior to their use in a dual-analyte immunoassay, in order that the apparent RLU's can be corrected and the pure signal of each tracer detected by each PMT assembly be obtained when the two tracers were flashed simultaneously in the same tube.

Table VII shows the determined PCT's of several pairs of tracers. Anti-FSH-DMAE and anti-LH-LEAE were used in the simultaneous LH/FSH dual-analyte assay described below. Other pairs of tracers were included to demonstrate that through the selection of acridinium and benzacridinium compounds of wider separation in their emission maxima and proper choice of optical filters, minimal PCT's ideal for multi-analyte assay can be realized. The PCT's were obtained by dividing the minor signal from the secondary PMT by the major signal from the primary PMT in each case, and multiplying the results by 100%.

The concentrations of the samples were randomly selected such that the primary signals fell in the range of 100,000 to 1,500,000 RLU's per 25 ul sample. Each determination was made by sequencially pipeting 25 ul of one tracer solution, 300 ul of Flashing Reagent #1 into the cuvette, vortexing the resulting solution briefly, inserting the cuvette into the PMT housing, and performing the flashing by injecting 300 ul of Flashing Reagent #2 through the key-board control.

TABLE VII

Determination of Percent Cross-Talk (PCT)

| Sample | Long Pass Signals (RLU's) | Short Pass Signals (RLU's) | PCT (%) |
|---|---|---|---|
| SET (I)*: | | | |
| LH tracer | 538 | 688 | |
| diluent | 444 | 396 | |
| Anti-LH—LEAE | 6.25 E5 | 4.18 E4 | 6.7 |
| | 5.78 E5 | 3.91 E4 | 6.8 |
| | 6.19 E5 | 4.18 E4 | 6.8 |
| | | | Aver. 6.8 |
| FSH tracer | 242 | 288 | |
| diluent | 268 | 340 | |
| Anti-FSH—DMAE | 2.32 E4 | 1.59 E5 | 14.5 |

TABLE VII-continued

Determination of Percent Cross-Talk (PCT)

| Sample | Long Pass Signals (RLU's) | Short Pass Signals (RLU's) | PCT (%) |
|---|---|---|---|
| | 2.42 E4 | 1.65 E5 | 14.7 |
| | 2.60 E4 | 1.75 E5 | 14.8 |
| | | | Aver. 14.7 |
| SET (II)^: | | | |
| Anti-LH—LEAE | 1.27 E6 | 5.52 E4 | 4.4 |
| | 1.25 E6 | 5.40 E4 | 4.3 |
| | | | Ave. 4.4 |
| Anti-FSH—DMAE | 4.62 E4 | 4.28 E5 | 10.8 |
| | 4.60 E4 | 4.23 E5 | 10.9 |
| | | | Ave. 10.9 |
| SET (III)+: | | | |
| Buffer~ | 348 | 278 | |
| | 350 | 284 | |
| Anti-TSH-2-MeO—LEAE | 9.90 E5 | 1.29 E4 | 1.3 |
| | 9.88 E5 | 1.29 E4 | 1.3 |
| | | | Ave. 1.3 |
| Anti-FSH—DMAE | 1.17 E4 | 3.77 E5 | 3.1 |
| | 1.17 E4 | 3.81 E5 | 3.1 |
| | | | Ave. 3.1 |
| SET (IV)#: | | | |
| Buffer~ | 187 | 608 | |
| | 182 | 429 | |
| Anti-TSH-2-MeO—LEAE | 2.12 E5 | 6.26 E3 | 2.9 |
| | 2.0 E5 | 5.95 E3 | 2.9 |
| | | | Aver. 2.9 |
| Anti-TSH—DMAE | 2.93 E4 | 5.39 E5 | 5.4 |
| | 3.12 E4 | 5.83 E5 | 5.4 |
| | | | Aver. 5.4 |

*Optical filters mounted on the DPL: LL-500 & P70-450.
^Optical filters mounted on the DPL: LL-500 & Laminated CS-550/CS-600.
+Optical filters mounted on the DPL: LL-520 & Laminated CS-500/CS-600.
Optical filters mounted on the DPL: LL-520 & P70-450.
~The buffer was 10 mM PBS/0.1% BSA/0.05% NaN$_3$, pH 8.0.

The constancy of the PCT over a wide range of RLU's is critical in the multi-analyte assay signal correction. Table VIII shows that when the laminated CS550/CS600 filter and LL520 filter were used to gate the short pass and long pass signals, respectively, the PCT for anti-TSH-DMAE has the mean of 2.96% with standard deviation of 0.16% over RLU range of 10,000 to 7,000,000 counts or broader, while the PCT for anti-CKMB-LEAE has the mean of 4.79% with standard deviation of 0.23% over RLU range of 50,000 to 7,000,000 counts or broader.

TABLE VIII

Constancy of Percent Cross-Talk

| Sample | Short Pass Signal (RLU's) | Long Pass Signal (Rlu's) | PCT (%) | Mean/SD (%) |
|---|---|---|---|---|
| Anti-TSH—DMAE | 6,689,796 | 217,010 | 3.24 | |
| | 6,545,872 | 212,956 | 3.25 | |
| | 6,645,674 | 210,262 | 3.16 | |
| | 1,469,500 | 43,710 | 2.97 | |
| | 1,469,770 | 45,004 | 3.06 | |
| | 1,450,042 | 43,492 | 3.00 | |
| | 303,944 | 8,922 | 2.81* | |
| | 302,876 | 8,788 | 2.78* | |
| | 287,632 | 8,928 | 2.98* | |
| | 59,468 | 2,106 | 2.95* | |
| | 58,816 | 2,072 | 2.93* | |
| | 60,314 | 1,996 | 2.73* | |
| | 12,298 | 692 | 2.77* | |
| | 11,956 | 692 | 2.86* | |
| | 12,420 | 716 | 2.96* | 2.96/0.16 |
| Buffer Diluent | 738 | 496 | | |
| | 702 | 320 | | |
| Anti-CKMB—LEAE | 320,758 | 6,663,484 | 4.81 | |
| | 315,344 | 6,497,756 | 4.85 | |
| | 320,224 | 6,528,242 | 4.91 | |
| | 61,374 | 1,350,584 | 4.54 | |
| | 61,514 | 1,329,548 | 4.63 | |
| | 60,036 | 1,330,152 | 4.51 | |
| | 13,044 | 264,526 | 4.71* | |
| | 11,968 | 244,106 | 4.67* | |
| | 12,324 | 245,542 | 4.78* | |
| | 3,312 | 56,120 | 4.84* | |
| | 3,586 | 54,906 | 5.45* | |
| | 3,220 | 53,928 | 4.87* | 4.79/0.23 |
| Buffer Diluent | 652 | 372 | | |
| | 622 | 346 | | |

*Correction was made in consideration of the additional signal contributed by the buffer and system noise.

Equations for Correcting the Apparent RLU's due to Cross-Talks in Dual-Tracer Determination When DMAE and LEAE derivatives or tracers are mixed and flashed simultaneously, the observed long and short pass signals can be broken down as follows:

$$S(s) = S(DMAE) + S'(LEAE) + b1 \quad (1)$$

$$S(l) = S(LEAE) + S'(DMAE) + b2 \quad (2)$$

Where, S(s) and S (l) are the observed short and long pass signals, respectively; S(DMAE) and S(LEAE) are the portions of signals due to DMAE and LEAE in the observed short and long pass signals, respectively. They will also be referred to as the corrected DMAE and LEAE signals; S' (DMAE) and S' (LEAE) are portions of the long and short pass signals due to DMAE and LEAE cross-talking, respectively; b1 and b2 are the combined signals due to assay components and system noise in the absence of DMAE and LEAE tracers, respectively.

Since the PCT's (represented by k1 and k2 below) are constants for any particular DMAE and LEAE tracers, there exist the following relationships:

$$S'(DMAE) = k1 \times S(DMAE) \quad (3)$$

$$S'(LEAE) = k2 \times S(LEAE) \quad (4)$$

Where k1, k2 are the PCT's for the DMAE and LEAE tracers, respectively.

Substitute equation (4) into (1):

$$S(s) = S(DMAE) + k2 \times S(LEAE) + b1 \text{ or}$$
$$S(DMAE) = S(s) - k2 \times S(LEAE) - b1 \quad (5)$$

Substitute equations (5) into (3) and (3) into (2):

$$S(l) = S(LEAE) + k1 \times [S(s) - k2 \times S(LEAE) - b1 + b2 = S(LEAE) + k1 \times S(s) - S(s) - k1 \times k2 \times S(LEAE) - k1 \times b1 + b2$$

$$S(l) - k1 \times S(s) + k1 \times b1 - b2 = S(LEAE) - k1 \times k2 \times S(LEAE) \quad (6)$$
$$= S(LEAE) \times (1 - k1 \times k2)$$

$$S(LEAE) = \frac{S(l) - k1 \times S(s) + k1 \times b1 - b2}{1 - k1 \times k2}$$

Equations (5) and (6) will yield the corrected short pass signal due to DMAE tracer and long pass signal due to LEAE tracer, respectively. For the purpose of demonstrating the feasibility of conducting a simultaneous LH/FSH dual-analyte assay, the determination of the combined matrix and system noises, b1 and b2 was found not to be significant. They were therefore both assigned a 0 value in the signal corrections for the following examples of the dual-analyte assays.

Simultaneous Immunoassay for Luteinizing Hormone (LH) and Follicle Stimulating Hormone (FSH):

One objective of the invention is to provide a method for simultaneously detecting and/or quantitating two or more substances or analytes in a single sample through the utilization of two different chemiluminescent labels or conjugates.

In an example of one embodiment, the assay system utilizes a DMAE labelled FSH antibody and a LEAE labelled LH antibody. The following examples demonstrate that LH and FSH standard curves and sample recovery are identical within the limits of experimental error when each analyte is assayed as a single analyte by introduction of one chemiluminescent tracer into the assay system, or in a dual analyte system which employs two chemiluminescent tracers. The examples further show that tracers prepared from a pair of a DMAE and a LEAC can be utilized in a simultaneous assay of two substances for which a corresponding binding partner, e.g. antibody, is available.

Example 15. Single FSH assay using Dual-Analyte Immunoassay System

The Magic Lite FSH kit components and protocol (Ciba Corning Diagnostics) were modified such that the assay could be performed as a single or dual analyte assay depending on the tracer selection. A solid phase consisting of paramagnetic particles (PMP) coupled to anti-FSH antibodies and PMP coupled to anti-LH antibodies was prepared by removing the buffer diluent from the Magic Lite FSH kit solid phase and resuspending these particles in Magic Lite LH kit solid phase (Ciba Corning Diagnostics Corp.). The kit tracer, anti-FSH-DMAE, was diluted 1:2 in Magic Lite LH kit tracer buffer. Standards for calibration contained both FSH and LH. Standards were prepared by spiking known concentrations of purified human FSH and human LH into a horse serum basepool. Nominal standard values were 0, 0.9, 2.2, 4.4, 8.8, 21.9, 43.8, 87.5, 140.0, 201.0 mIu/ml of FSH. Nominal LH concentrations were 0, 1.0, 2.5, 5.0, 10.0, 25.0, 50.0, 100.0, 160.0, 230.0 mIu/ml LH. Samples for analysis were prepared by spiking a human serum pool with varying concentrations of both purified human FSH and human LH. Additionally, serum based multi-constituent calibrators containing human FSH and human LH were used as samples.

To perform the assay, 50 ul of each standard or sample and 200 ul of diluted FSH tracer were vortex mixed and incubated for 30 minutes at room temperature. 500 ul of the combined anti-FSH/anti-LH solid phase was added, vortex mixed and incubated for 30 minutes at room temperature. The reacted solid phase was magnetically separated for 3 minutes in a Magic Lite rack (Ciba Corning Diagnostics Corp.), see European Patent 136126, and the supernatant decanted. The reacted solid phase was next washed with 1.0 ml of distilled water, separated for 3 minutes. The supernatant was decanted, and 100 ul of distilled water added. Each sample was manually transferred to a cuvette, and counted for 5 seconds on the DPL described above. The results (in RLU's) obtained from the short pass (DMAE) channel were used to calculate FSH concentration in each sample. Concentrations were calculated by using 10-point calibration with a spline data reduction routine. Each standard and sample was assayed in replicates of three. RLU's and %CVC for this assay are shown in Table IX under the heading FSH single-analyte assay. FSH sample recovery is shown in Table X under the heading FSH single-analyte assay. The FSH standard curve presented as %B/Bmax vs log FSH concentration is shown in FIG. 8 labelled as FSH single-analyte assay.

Example 16. Single LH Assay using Dual-analyte Immunoassay System

The solid phase reagent, standards, and samples described in Example 15 were used to perform an LH assay. The anti-FSHDMAE tracer was replaced with an anti-LH-LEAE tracer which was diluted 1:2 in Magic Lite FSH kit tracer diluent. The assay methodology described in Example 13 was applied to this assay, except that the RLU results obtained from the Long pass (LEAE) channel were used to calculate LH sample concentrations.

Figure 9:
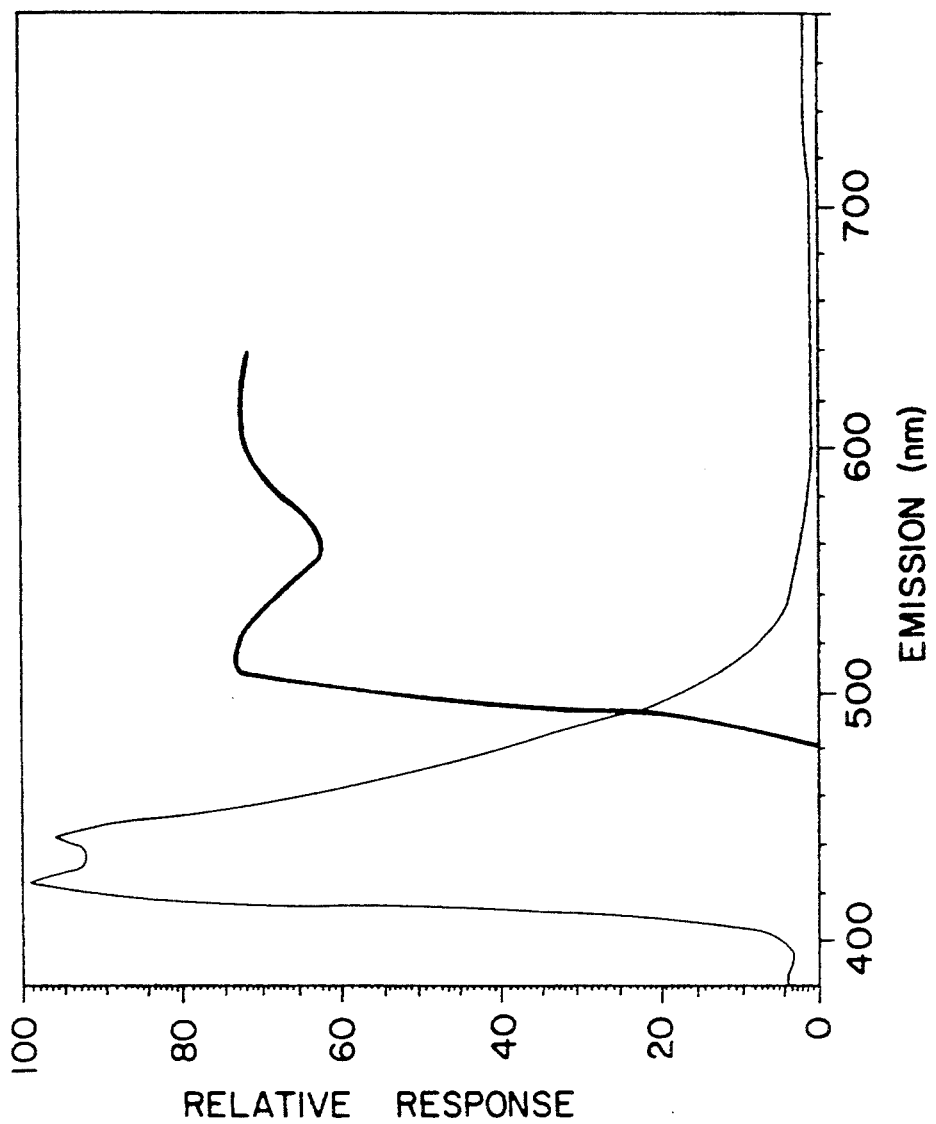
FIG. 9 illustrates the area of overlap between the transmittance curve of an optical filter (Corion LL500) and the emission spectra of DMAE-Bz.
Figure 10:
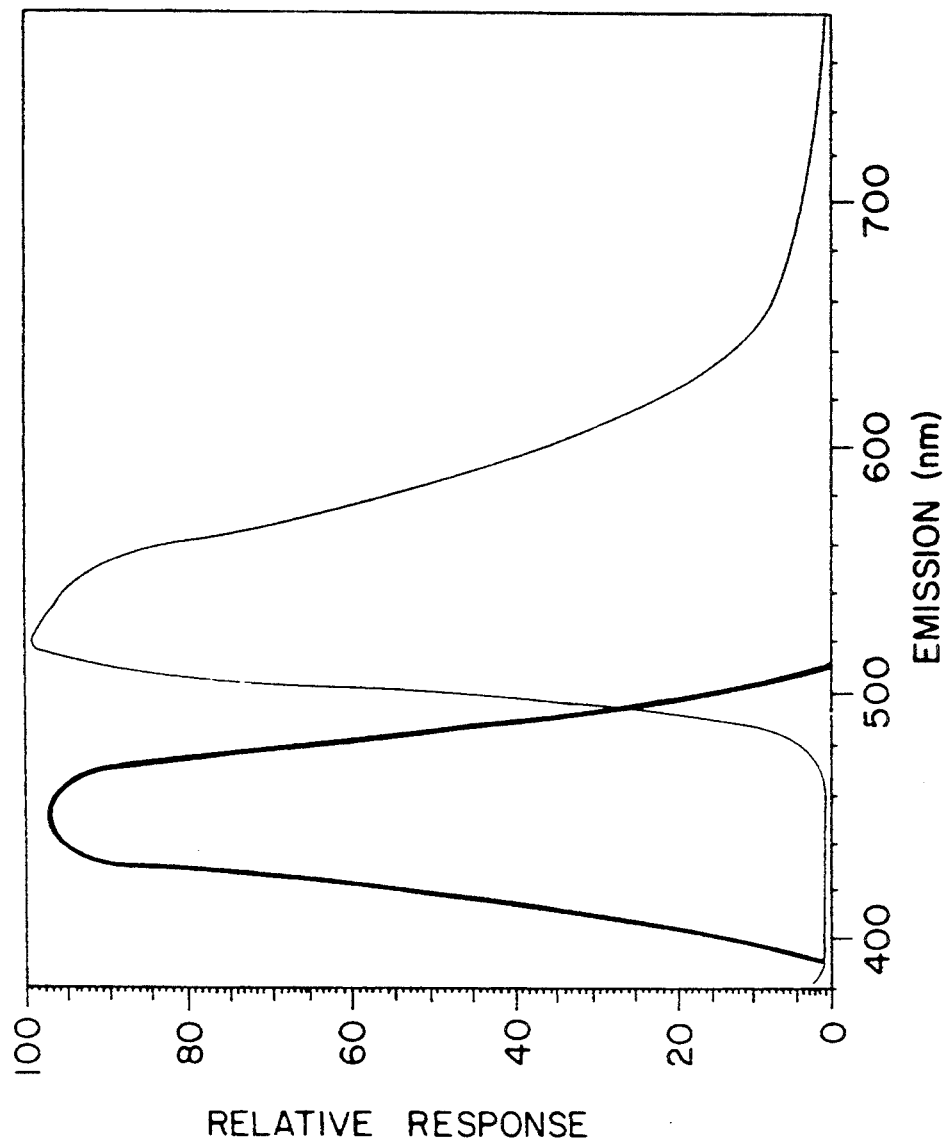
FIG. 10 illustrates the area of overlap between the transmittance curve of an optical filter (Corion P70-450) and the emission spectra of LEAE-Bz.
Figure 11:
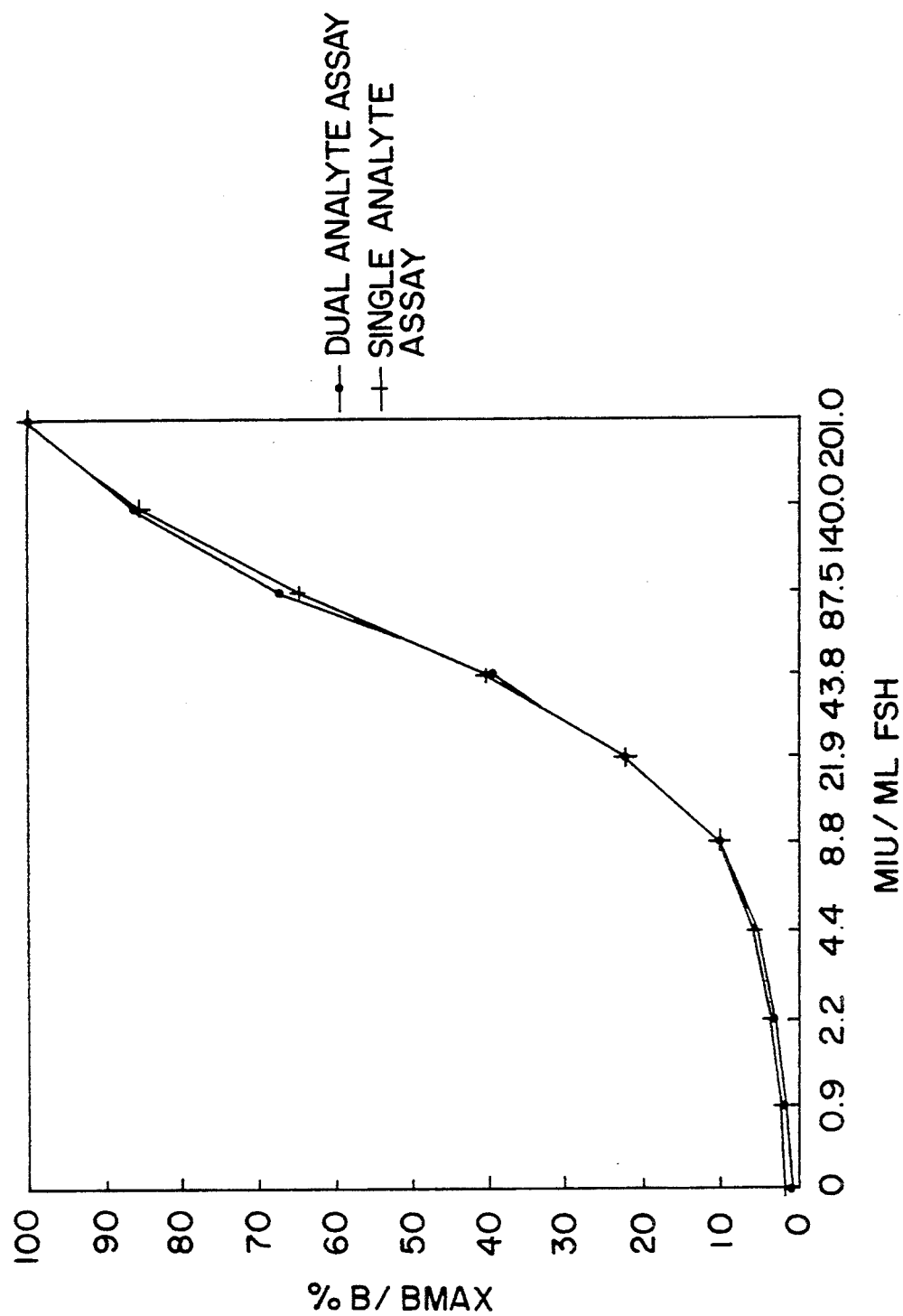
FIG. 11 illustrates FSH standard curve assays read on a dual PMT luminometer.

The assay was calibrated using nine of the standards described in Example 15, excluding the 1.0 mIu/ml LH standard. Results for this assay are shown in Table XI and Table XII under the heading LH single-analyte assay. The standard curve is shown in FIG. 9 labelled as LH single-analyte assay.

Example 17. Simultaneous LH/FSH Assay using Dual-analyte Immunoassay System

Solid phase reagent, standards, and samples described in Example 15 and 16 were used to perform a dual label LH/FSH assay in a single tube. The tracer consisted of the Magic Lite FSH kit tracer, anti-FSH-DMAE diluted 1:2 in the anti-LH-LEAE tracer. The assay methodology was the same as that described in Example 15. The raw RLU's from each channel was mathematically corrected for cross-talk prior to concentration calculations. Corrected RLU's and concentrations resulting from these corrected RLU's are shown in Tables IX-XII, and are labelled as dual-analyte assay. Mean sample recovery for single analyte vs. dual analyte assays are compared by t-test in Tables X-XII. The FSH and LH standard curves are shown in FIGS. 8 and 9 and labelled as FSH and LH dual-analyte assay, respectively.

Assays and Assay Formats

The present invention relates to chemiluminescent compounds and more particularly, the use of two or more chemiluminescent conjugates to simultaneously detect two or more substances in a test sample. The disclosure teaches the use of benzacridinium compounds and preferably N-alkylated benzacridinium compounds in such assays.

A test substance includes any component(s) or analytes sought to be detected and/or quantitated in a test sample, including but not limited to, more than one component of a single structure, e.g. more than one portion of a nucleic acid sequence or different loci of a chromosome, genome or molecule, where the components or analytes may be of biological or industrial origin, such as nucleic acids, proteins, ligands, haptens or other materials or compounds to which an appropriate assay method can be formatted. It is understood that the test sample and/or substance may need to be pretreated to render it assayable by a test method. The test substances and quantities thereof sought to be detected may limit the types of assays which can be performed because of, for example, sensitivity concerns, but not the use of chemiluminescent labels for detection. Various internal standards or controls may be added to a test sample for detection and/or quantitation to asess the performance of the assay. Diagnostic assays exemplified by immunoassays, hybridization assays and amplification assays have increasingly incorporated chemiluminescent labels in their formats. Designs and formats of such assays are well known by those skilled in the art and extensively published in the technical and patent literature, for example, an assay format may require the seperation of a reaction product or unreacted agent to a transfer tube for detection and/or quantitation. Such separation techniques may be useful for competitive assays, solid phase assays or to limit interferents.

In one embodiment of the invention, two or more chemiluminescent conjugates are utilized as labels in an amplification assay. Representative amplification assays include but should not be limited to polymerase chain reaction (PCR), autocatalytic replication of recombinant RNA and amplification of midivariant DNA or RNA. See EP-A-O 481 704 (priority USSN No. 598,269 (10/16/90)) which is commonly assigned and incorporated herein by reference. Such methods, as taught in the technical and patent may be made adaptable to incorporate chemiluminescent labels, and particularly two or more chemiluminescent labels for detection of target sequences of interest. The advantage of using a multi-label method is to detect and/or quantitate a plurality of target sequences or one or more target sequences and an internal standard. An example of such a method includes providing a test sample suspected of containing one or more target sequences, amplifying the target sequences, providing at least two chemiluminescent conjugates, each chemiluminescent conjugate being associated with a target sequence(s) and simultaneously detecting and/or quantifying amplified target sequences by emissions of at least two chemiluminescent conjugates. In another step of this method an internal reference, control or control system may be added to the assay to insure assay performance and results. The internal reference may be amplified as well as the target sequences.

The use of chemiluminescent labels for such assays serves to demonstrate the utility of this invention.

The chemiluminescent compounds of this invention are adapted to be packaged in kit form for commercial sale. The chemiluminescent labels of these kits may be conjugated to appropriate substances or materials which are specific to the substances sought to be detected in the test samples. Appropriate functional groups may be added to the chemiluminescent compounds for use in various assays and other applications. Examples of assays for which the methods of the present invention may be utilized include but should not be limited to: assays including at least two antibodies of different specifities; assays including at least two antigens; assays including at least one antigen and at least one antibody; and assays for molecules indicative of cancer, infectious diseases, genetic abnormalities, genetic disposition, genetic assessment and to monitor medicinal therapy.

It is to be understood that various other modifications will be apparent to and can readily be made by those skilled in the art, given the disclosure herein, without departing from the scope and materials of this invention. It is not, however, intended that the scope of the claims appended hereto be limited to the description as set forth herein, but rather that the claims be construed as encompassing all features of patentable novelty which reside in the present invention, including all features which would be treated as equivalents thereof by those skilled in the art to which the invention pertains. It is also noted that the examples given therein are intended to illustrate, and not to limit the invention.

TABLE IX

| | MEAN RLU's and % CVC FOR MODIFIED MAGIC LITE FSH ASSAYS | | | |
|---|---|---|---|---|
| | FSH SINGLE ANALYTE ASSAY | | FSH RESULTS DUAL ANALYTE ASSAY* | |
| SAMPLE (VALUE) | MEAN RLU | % CVC | MEAN RLU | % CVC |
| S1 (0) | 1336 | 4.3 | 610 | 6.7 |
| S2 (0.9) | 1891 | 5 | 1309 | 14.4 |
| S3 (2.2) | 3202 | 10.9 | 2375 | 6.7 |
| S4 (4.4) | 5155 | 9.4 | 4189 | 3.9 |
| S5 (8.8) | 9005 | 2.6 | 7702 | 2.4 |
| S6 (21.9) | 19637 | 5.5 | 16942 | 5.2 |
| S7 (43.8) | 35491 | 0.7 | 30563 | 4 |
| S8 (87.5) | 56844 | 1.7 | 51969 | 5 |
| S9 (140.0) | 74850 | 0.9 | 66499 | 0.5 |
| S10 (201.0) | 87531 | 0.8 | 77003 | 0.5 |
| SAMPLE 1 | 9962 | 7.3 | 8417 | 2.8 |
| SAMPLE 2 | 16779 | 4.9 | 14777 | 0.8 |

TABLE IX-continued

MEAN RLU's and % CVC FOR MODIFIED MAGIC LITE FSH ASSAYS

| SAMPLE (VALUE) | FSH SINGLE ANALYTE ASSAY | | FSH RESULTS DUAL ANALYTE ASSAY* | |
|---|---|---|---|---|
| | MEAN RLU | % CVC | MEAN RLU | % CVC |
| SAMPLE 3 | 29683 | 13 | 28721 | 4.5 |
| SAMPLE 4 | 62549 | 2.2 | 55878 | 2.4 |
| SAMPLE 5 | 93019 | 1.1 | 84182 | 3.3 |
| SAMPLE 6 | 103290 | 3 | 93297 | 1.2 |
| LOW MULTI-CAL | 1756 | 9 | 1160 | 9.8 |
| HIGH MULTI-CAL | 80308 | 2.4 | 71082 | 0.6 |
| TOTAL COUNTS | 564200 | | 571392 | |

*corrected RLU

TABLE X

FSH SAMPLE RECOVERY: SINGLE ANALYTE ASSAY VS. DUAL ANALYTE ASSAY

| SAMPLE | FSH SINGLE ANALYTE ASSAY | | FSH DUAL ANALYTE ASSAY | | T-VALUE | CRITICAL T-VALUE 95% C.I. |
|---|---|---|---|---|---|---|
| | MIU/ML | % CVD | MIU/ML | % CVD | | |
| SAMPLE 1 | 9.923 | 8.6 | 9.737 | 3.2 | 0.36 | +/−4.30 |
| SAMPLE 2 | 18.291 | 5.7 | 18.668 | 1 | −0.62 | +/−4.30 |
| SAMPLE 3 | 35.235 | 15.1 | 40.708 | 5.3 | −1.65 | +/−4.30 |
| SAMPLE 4 | 101.951 | 3.5 | 98.877 | 4.2 | 0.98 | +/−3.18 |
| SAMPLE 5 | >> | | >> | | | |
| SAMPLE 6 | >> | | >> | | | |
| MULTI-CAL LOW | 0.693 | 30.8 | 0.697 | 20.1 | −0.2 | +/−3.18 |
| MULTI-CAL HIGH | 163.132 | 5.4 | 163.812 | 1.4 | −0.13 | +/−4.30 |

TABLE XI

MEAN RLU'S AND % CVC FOR MODIFIED MAGIC LITE LH ASSAYS

| SAMPLE (VALUE) | LH SINGLE ANALYTE ASSAY | | LH RESULTS DUAL ANALYTE ASSAY* | |
|---|---|---|---|---|
| | MEAN RLU | % CVC | MEAN RLU | % CVC |
| S1 (0) | 17.883 | 14.2 | 18,477 | 10.6 |
| S3 (2.5) | 24,310 | 1.9 | 22,818 | 2.7 |
| S4 (5.0) | 27,007 | 6.5 | 25,118 | 11.9 |
| S5 (10.0) | 34,713 | 11.6 | 28,934 | 6.2 |
| S6 (25.0) | 42,440 | 4.6 | 41,543 | 5.3 |
| S7 (50.0) | 65,787 | 2.9 | 71,140 | 6.2 |
| S8 (100.0) | 115,760 | 6.8 | 113,694 | 1.9 |
| S9 (160.0) | 161,767 | 4.4 | 164,225 | 4.4 |
| S10 (230.0) | 223,569 | 4.8 | 205,347 | 4.5 |
| SAMPLE 4 | 42,157 | 2.8 | 40,519 | 8.2 |
| SAMPLE 5 | 82,934 | 4.3 | 83,592 | 5.5 |
| SAMPLE 6 | 110,502 | 2.8 | 113,285 | 1.9 |
| MULTI-CAL HIGH | 86,189 | 3.5 | 90,451 | 2.9 |
| TOTAL COUNTS | 2,250,526 | | 2,322,672 | |

*CORRECTED RLU

TABLE XII

LH SAMPLE RECOVERY: SINGLE ANALYTE ASSAY VS. DUAL ASSAY

| SAMPLE | LH SINGLE ANALYTE ASSAY | | LH RESULTS DUAL ANALYTE ASSAY* | | T-VALUE | CRITICAL T-VALUE 95% C.I. |
|---|---|---|---|---|---|---|
| | MIU/ML | % CVD | MIU/ML | % CVD | | |
| SAMPLE 4 | 21.347 | 7 | 22.342 | 15.3 | −0.46 | +/−4.30 |
| SAMPLE 5 | 67.392 | 5.7 | 64.829 | 7.5 | 0.72 | +/−3.18 |
| SAMPLE 6 | 97.375 | 3.6 | 97.984 | 2.5 | −0.25 | +/−3.18 |
| MULTI-CAL HIGH | 70.906 | 4.5 | 72.153 | 4 | −0.5 | +/−3.18 |

What is claimed is:

1. A luminometer for detecting chemiluminescence comprising:

a housing having top, bottom and sidewall regions disposed to form a chamber wherein the top region of said housing has an opening which leads to the chamber and wherein two opposing sidewall regions are each provided having a bore therethrough;

a reaction vessel, disposed in the chamber of said housing, said reaction vessel for holding a specimen sample and a first plurality of reagents;

a dispense assembly, disposed above said reaction vessel, said dispense assembly for dispensing at least one additional reagent to said reaction vessel, wherein the dispensing of the additional reagent to the specimen sample initiates a chemiluminescent reaction within said reaction vessel and results in emission of light energy in a plurality of predetermined spectral ranges at intensities independently related to plural specimen constituents or substances of the sample wherein said dispense assembly comprises:
  a probe body having a first end and a second end and having an opening therethrough; and
  at least one dispense probe disposed in the opening of said probe body; and
  a pair of detectors, each one of said pair of detectors disposed in a respective one of the bores in the two opposing sidewall regions wherein a first surface of each of said pair of detectors is disposed through the bores and exposed to said reaction vessel and wherein each of said pair of detectors detects a portion of the light emission from the chemiluminescent reaction in at least one of a plurality of predetermined spectral ranges: and
  means for centering said reaction vessel between said pair of detectors such that a centerline of said reaction vessel is equally spaced from the first surface of each of said pair of detectors.

2. The specimen testing apparatus of claim 1 wherein said means for centering comprises:
  a reaction vessel sensor assembly, disposed in the chamber, said reaction vessel sensor assembly including a member having a curved surface such that when a first surface of said reaction vessel contacts the curved surface of said member, said member centrally locates said reaction vessel in the chamber such that the centerline of said reaction vessel equally spaced from the first surface of each of said pair of detectors and wherein said reaction vessel sensor assembly also provides an indication that said reaction vessel is disposed in a predetermined position within the chamber.

3. The specimen testing apparatus of claim 2 further comprising:
  a cover coupled to said housing, wherein said cover moves between a first position in which the opening to the chamber is exposed and a second position in which said cover forms a light tight seal over the opening; and
  a cover sensor assembly, disposed on the top wall of said housing and coupled to said cover, for sensing and indicating whether said cover has been placed in a first one of an open or closed position independently of whether said reaction vessel is disposed in the chamber.

4. The specimen testing apparatus of claim 3 wherein said reaction vessel sensor assembly further comprises:
  a sensor; and
  a spring wherein said member is disposed over said spring, said member having a first surface opposite the curved surface wherein the first surface of said member contacts said spring and said spring exerts of a force on said member which causes said reaction vessel to protrude out of the chamber when the cover is placed in the first position and when said cover is placed in the second position, said cover forces said reaction vessel into the chamber and said member activates said sensor.

5. The instrument of claim 1 further comprising:
  processing circuitry coupled to each of said pair of detectors, wherein each of the detectors feeds a detector signal to the processing circuitry and said processing circuitry evaluates each of the detector signals fed thereto to provide data for the presence of a specific specimen constituent based upon the detected luminescence in each of the plurality of predetermined spectral ranges.

6. The instrument of claim 5 wherein said dispense probe comprises:
  a guide tube coupled to said probe body; and
  a dispense tube disposed in said quide tube.

7. The instrument of claim 6 further comprising a fluid injection system comprising:
  at least one fluid container;
  at least one like feed line coupled between each said fluid container and a corresponding one of said at least one dispense probe;
  at least one like pump coupled between each said fluid container and a corresponding feed line, wherein said pump aspirates fluid from respective said container and dispenses the fluid through the corresponding feed line and dispense probe into said reaction vessel.

8. The specimen testing apparatus of claim 7 further comprising a like plurality of filters, each of said filters disposed between said reaction vessel and a corresponding one of said detectors, wherein each of said filters is provided having a predetermined filter characteristic to provide a filtered signal to the corresponding detector.

9. A specimen testing apparatus comprising: a housing having top, bottom and side wall regions coupled to form a chamber wherein a first one of the top, bottom and side wall regions of said housing has an opening therein which leads to the chamber:
  a reaction vessel disposed through the opening in the first one of the top, bottom and side wall regions of said housing such that said reaction vessel is disposed in the chamber;
  a dispenser assembly, disposed in the reaction vessel, for adding a first plurality of reagents to the reaction vessel, wherein the addition of the reagents to the specimen sample initiates a reaction within the reaction vessel and results in emission of light energy in a corresponding plurality of predetermined spectral ranges;
  a plurality of detectors for detecting light emissions, each one of said detectors disposed through a corresponding bore provided in the side wall regions of said housing and exposed to said reaction vessel;
  a reaction vessel sensor assembly disposed in the chamber wherein a first surface of said reaction vessel contacts said reaction vessel sensor assembly; add
  a like plurality of filters, each of said filters disposed between said reaction vessel and a corresponding one of said plurality of detectors wherein each of said filters is provided having a predetermined filter characteristic to provide a filtered signal to the corresponding detector and wherein said reaction vessel sensor assembly centrally locates said reaction vessel within the chamber such that a centerline of said reaction vessel is substantially equidistant from each of said plurality of detectors and wherein said reaction vessel sensor assembly provides a signal when said reaction vessel is located in the chamber such that a test may be performed.

10. The specimen testing apparatus of claim 9 wherein said detectors are disposed in diametrically opposing pairs about said reaction vessel.

11. The specimen testing apparatus of claim 10 wherein each of said detectors comprises a photomultiplier tube.

12. The specimen testing apparatus of claim 9 wherein said dispense assembly comprises:
   a dispensing probe having a first end disposed inside said reaction vessel and having a second end; and
   a pump having an output port coupled to the second end of said dispensing probe, for aspirating fluid from a container and dispensing the aspirated fluid through said dispensing probe and into the reaction vessel.

13. The specimen testing apparatus of claim 12 wherein said dispensing probe is a first one of a plurality of dispensing probes and said pump is a first one of a like plurality of pumps, each of said pumps having an output port coupled to a second end of each of said plurality of dispensing probes, and each of said pumps for aspirating fluid from one of a plurality of containers and dispensing the aspirated fluid through the probe and into the reaction vessel.

14. The specimen testing apparatus of claim 9 further comprising:
   a top cover assembly, disposed over the opening in said housing through which said reaction vessel is disposed and coupled to said dispense assembly, said top cover assembly for holding said dispense assembly in a predetermined location of said reaction vessel; and
   wherein said dispense assembly includes at least one dispense probe having at least a portion thereof disposed in said reaction vessel.

15. The specimen testing apparatus of claim 4 further comprising:
   a cover sensor assembly, disposed on the top wall of said housing and coupled to said top cover assembly, wherein said cover sensor assembly senses whether said top cover assembly has been placed in a first one of an open or closed position.

16. The specimen testing apparatus of claim 15 further comprising:
   a detection circuit coupled to said cover sensor assembly and said reaction vessel sensor assembly for detecting and indicating, after a first test has been performed and completed in said testing apparatus, a first one of the following conditions;
      (a) the cover has been opened and the reaction vessel has been removed;
      (b) the cover has been opened and the reaction vessel has not been removed; and
      (c) the cover has not been opened; and wherein when said detection circuit detects condition (b), said detection circuit prevents operation of the specimen testing apparatus: and
   wherein when said detection circuit detects condition (c), said detection circuit prevents operation of the specimen testing apparatus.

17. An instrument for detecting luminescence comprising:
   a housing having a reaction vessel chamber and having an opening through a wall of said housing wherein the opening leads to the chamber;
   a reaction vessel, disposed in the reaction vessel chamber of said housing, said reaction vessel for holding a specimen sample; a dispense assembly disposed to inject a reagent into said reaction vessel;
   a pair of detectors, coupled to said housing, wherein portions of each of said pair of detectors are disposed through said housing and are exposed to said reaction vessel and each of said detectors detect a portion of the light emission in one of a plurality of predetermined spectral ranges; and
   means for centering said reaction vessel between said pair of detectors.

18. The instrument of claim 17 further comprising:
   processing circuitry coupled to each of said pair of detectors, wherein each of the detectors feeds a detector signal to the processing circuitry and said processing circuitry evaluates each of the detector signals fed thereto to provide data for the presence of a specific specimen constituent based upon the detected luminescence in each of the plurality of predetermined spectral ranges.

19. The instrument of claim 18 wherein said dispense assembly comprises:
   a plurality of dispense probes, each of said plurality of dispense probes adapted for dispensing a reagent into said reaction vessel, wherein the addition of the reagents to the specimen sample initiates a chemiluminescent reaction within said reaction vessel and results in emission of light energy in a corresponding plurality of predetermined spectral ranges at intensities independently related to plural specimen constituents or substances of the sample.

20. The instrument of claim 19 wherein said plurality of reagents and said pair of detectors are provided as like pairs.

21. The instrument of claim 20 further comprising a fluid injection system comprising:
   a plurality of fluid containers;
   a like plurality of feed lines, each of said feed lines coupled between one of said plurality of fluid containers and a corresponding one of said plurality of dispense probes;
   a like plurality of pumps, each of said pumps coupled between one of said fluid containers and a corresponding one of said plurality of feed lines, wherein each of said pumps aspirate fluid from respective ones of said containers and dispense the fluid through the corresponding feed lines and dispense probes into said reaction vessel.

22. The instrument of claim 21 further comprising a like plurality of filters, each of said filters disposed between said reaction vessel and a corresponding one of said detectors, wherein each of said filters is provided having a predetermined filter characteristic to provide a filtered signal to the corresponding detector.

23. The instrument of claim 22 further comprising:
   a reaction vessel sensor assembly, disposed on a bottom surface of the chamber wherein when a first surface of said reaction vessel contacts said reaction vessel sensor assembly, said reaction vessel sensor assembly provides an indication that said reaction vessel is disposed in a predetermined position within said housing chamber.

24. The instrument of claim 23 wherein said reaction vessel sensor assembly comprising:
   a sensor;
   a spring; and
   a sensor flag disposed over said spring, said sensor flag having a first surface which the first surface of said reaction vessel contacts wherein said spring exerts a force which causes said reaction vessel to protrude out of the chamber and when said cover is placed in the second position, said cover forces said reaction vessel into the chamber and said sensor flag activates said sensor.

* * * * *